// United States Patent ///

(12) United States Patent
Moor et al.

(10) Patent No.: US 7,578,972 B2
(45) Date of Patent: Aug. 25, 2009

(54) FLUID ANALYSER SYSTEMS

(75) Inventors: Timothy Nicholas Moor, Gateshead (GB); Jonathan Alexander Redecen Dibble, Gateshead (GB)

(73) Assignee: Elan Vital (UK) Ltd (GB)

( * ) Notice: Subject to any disclaimer, the term of this patent is extended or adjusted under 35 U.S.C. 154(b) by 358 days.

(21) Appl. No.: 10/495,909

(22) PCT Filed: Nov. 21, 2002

(86) PCT No.: PCT/EP02/13177

§ 371 (c)(1),
(2), (4) Date: Oct. 12, 2004

(87) PCT Pub. No.: WO03/044503

PCT Pub. Date: May 30, 2003

(65) Prior Publication Data

US 2005/0063866 A1  Mar. 24, 2005

(30) Foreign Application Priority Data

Nov. 21, 2001  (GB)  .................................. 0127913.2

(51) Int. Cl.
*G01N 33/00* (2006.01)

(52) U.S. Cl. ........................ 422/82.05; 422/50; 422/55; 422/68.1

(58) Field of Classification Search ............... 422/82.05, 422/50, 55, 68.1
See application file for complete search history.

(56) References Cited

U.S. PATENT DOCUMENTS 6,114,178 A      9/2000   Dezael et al. ................ 436/180
2001/0039014 A1  11/2001  Crameri et al.

FOREIGN PATENT DOCUMENTS

WO    WO 9420013    9/1994
WO    WO 9826277    6/1998

*Primary Examiner*—Sam P Siefke
(74) *Attorney, Agent, or Firm*—Ohlandt, Greeley, Ruggiero & Perle, L.L.P.

(57) ABSTRACT

Fluid analyzer systems are provided which can detect a multitude of fluids in a sample to a very high level of accuracy which includes the detection of the presence of very small amounts of fluids. The results are both qualitative and quantitative. The systems consist of a receptacle which is filled with the fluid sample to be analysed which is placed into a consistent light condition environment where its temperature is measured. Under a predetermined time duration, Charge-Coupled Device (CCD) detector(s) receive by absorbance, radiation from the fluid sample at known wavelengths and are matched against a databank of known wavelengths of fluids. Matching wavelengths within a pre-defined tolerance will determine whether an individual fluid is present or not.

25 Claims, 35 Drawing Sheets

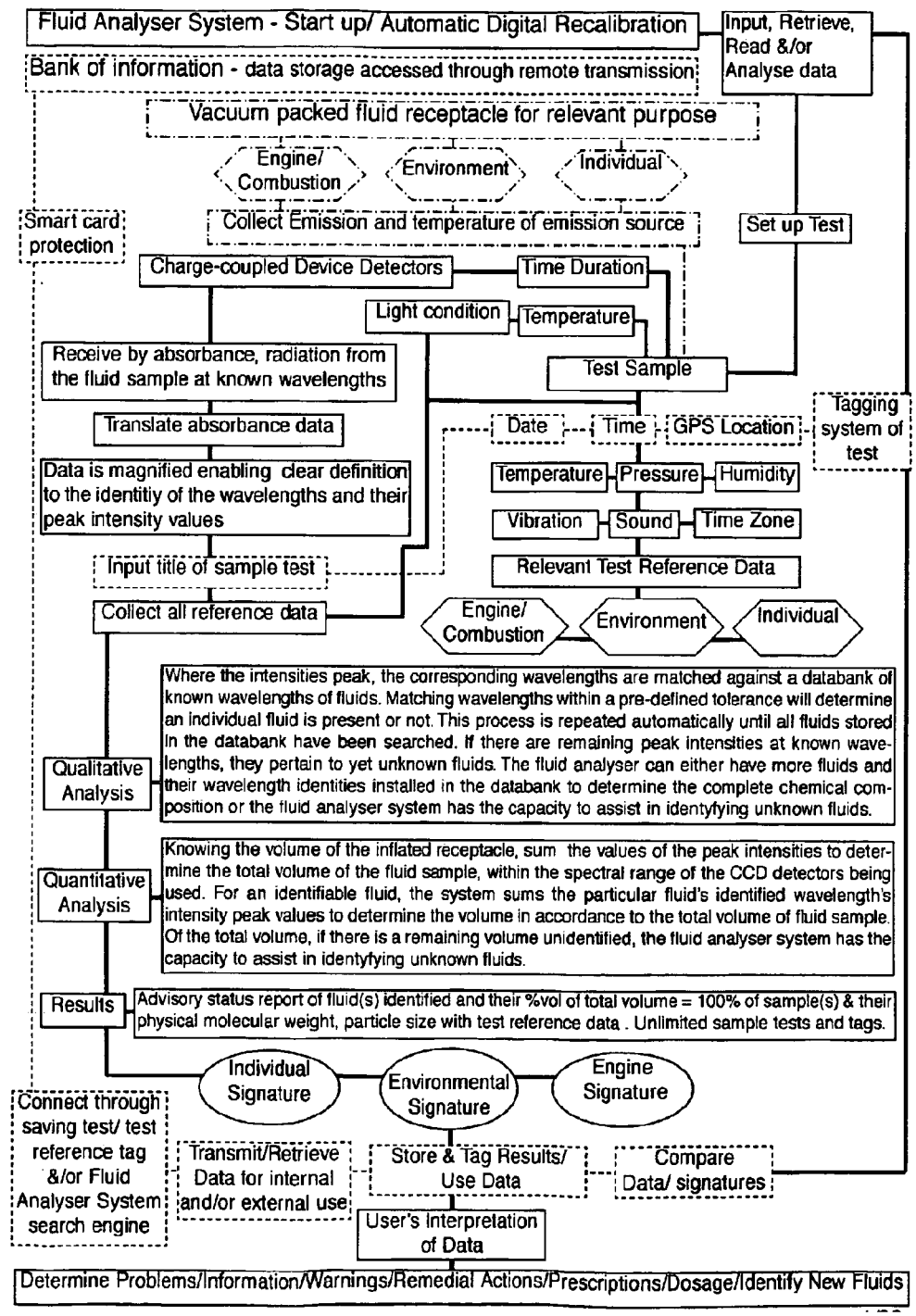
Figure 1. Schematic flow diagram of the performance of the system of the present invention

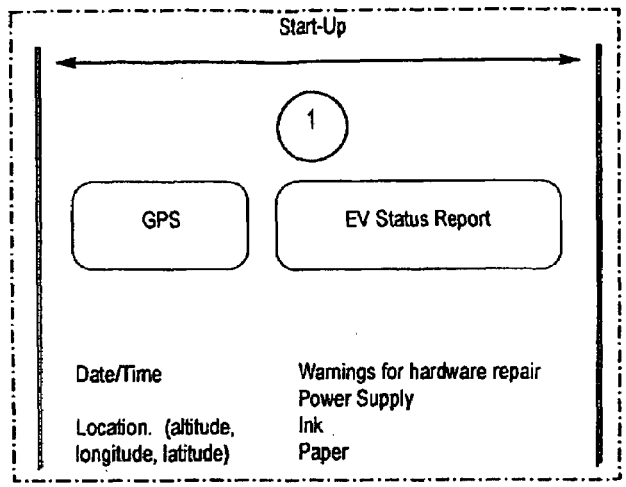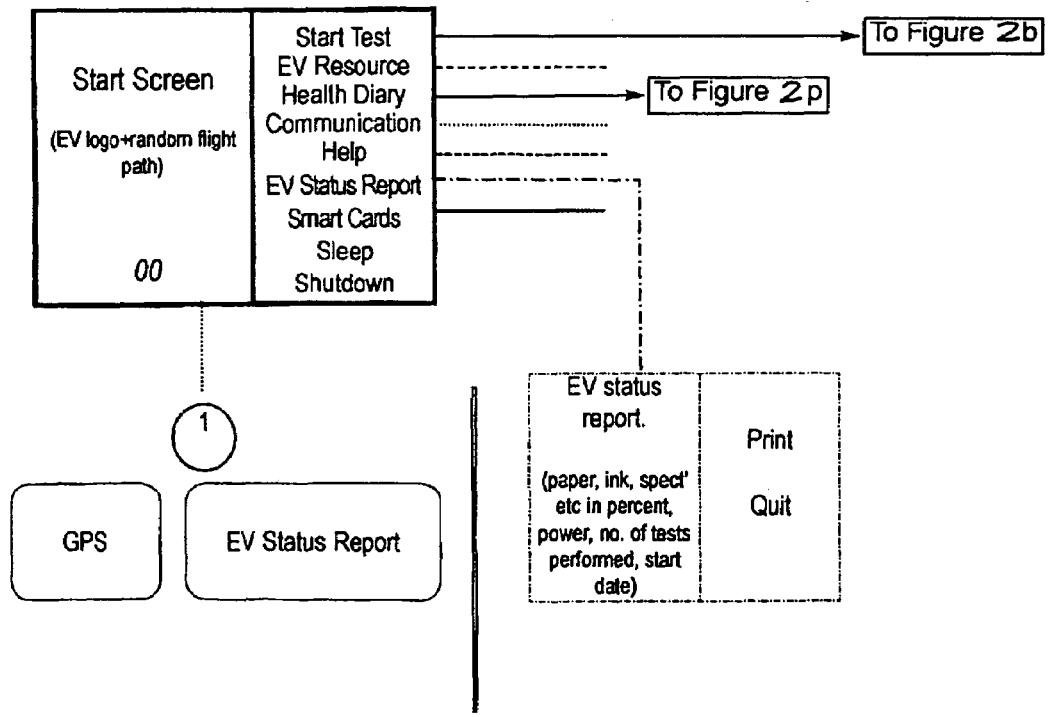
Fig. 2a

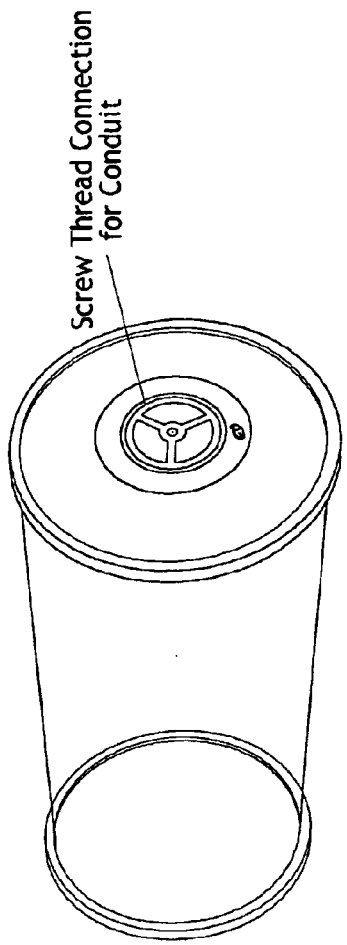
Figure 4
Screw Thread Connection for Conduit
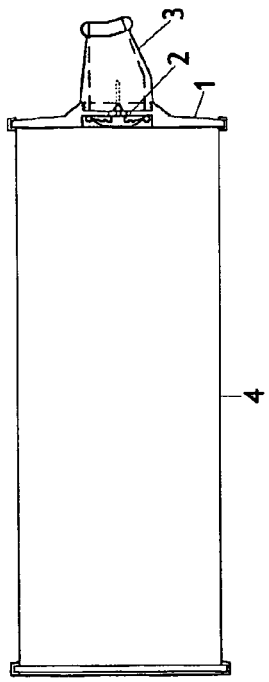
Figure 4a
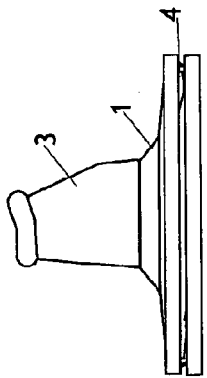
Figure 4b
Inflated
Figure 3
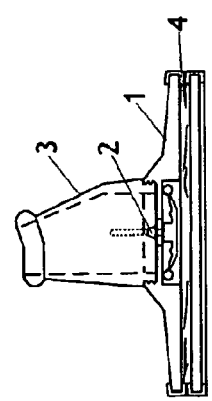
Uninflated - ready to Use

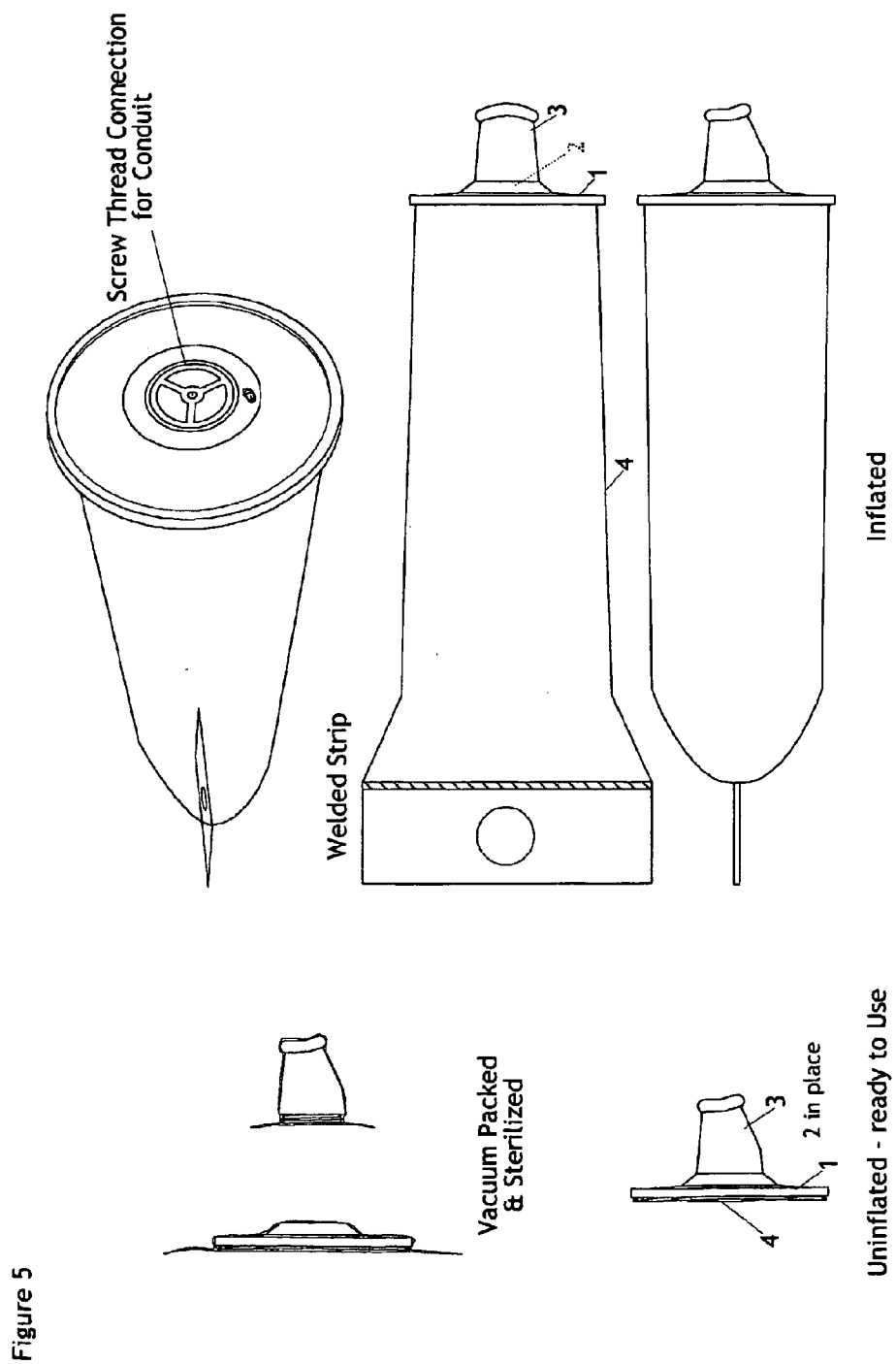

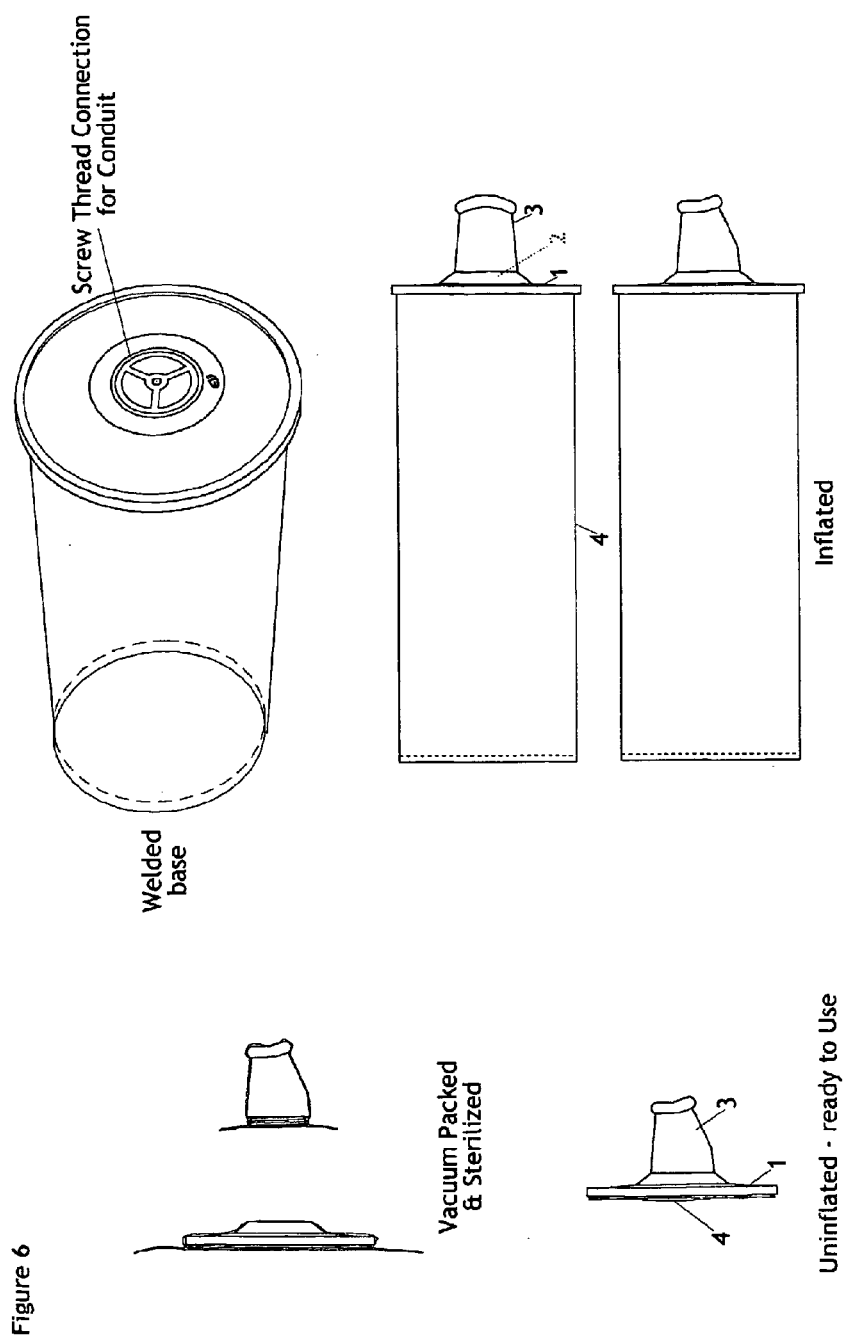

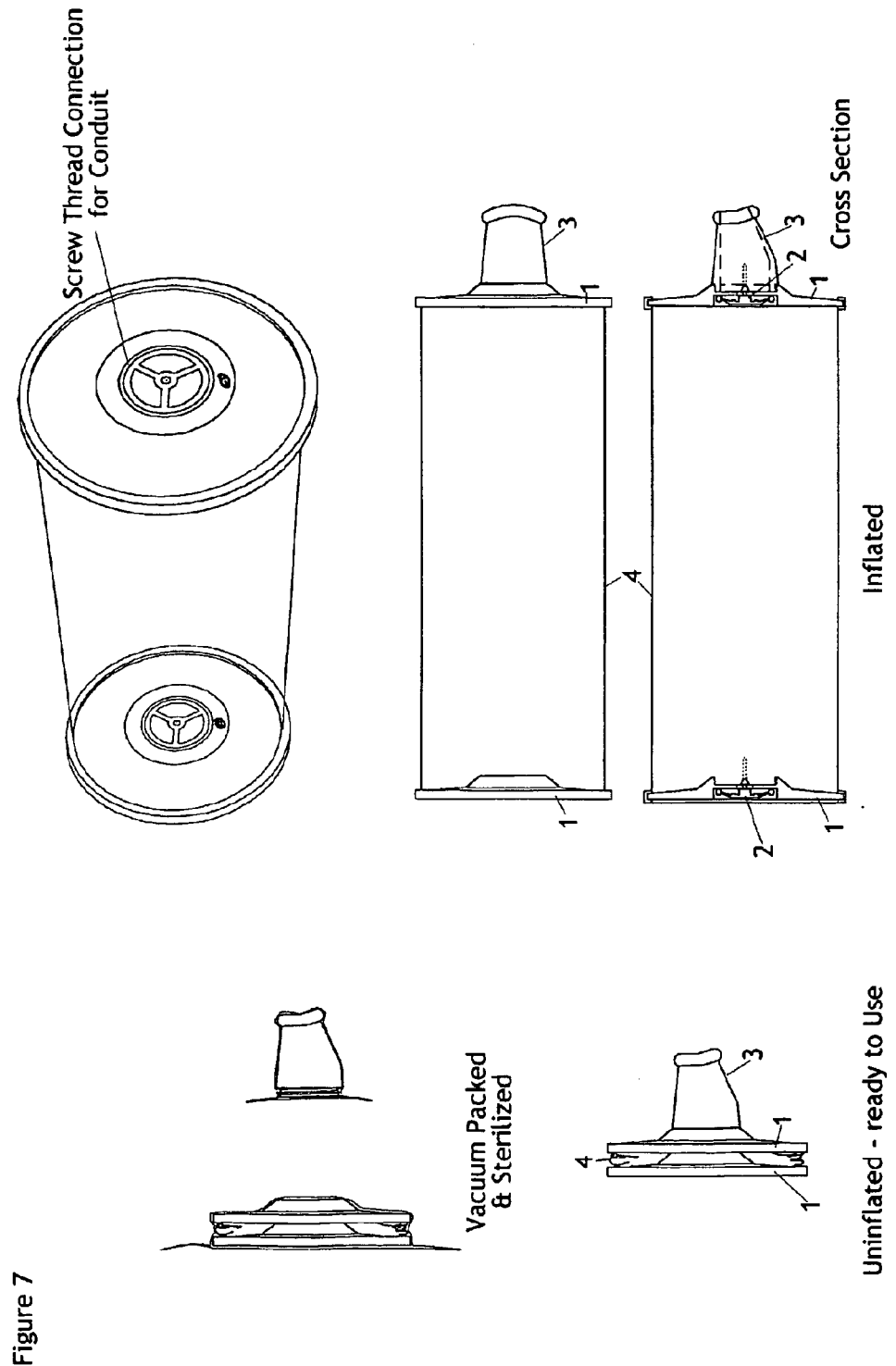

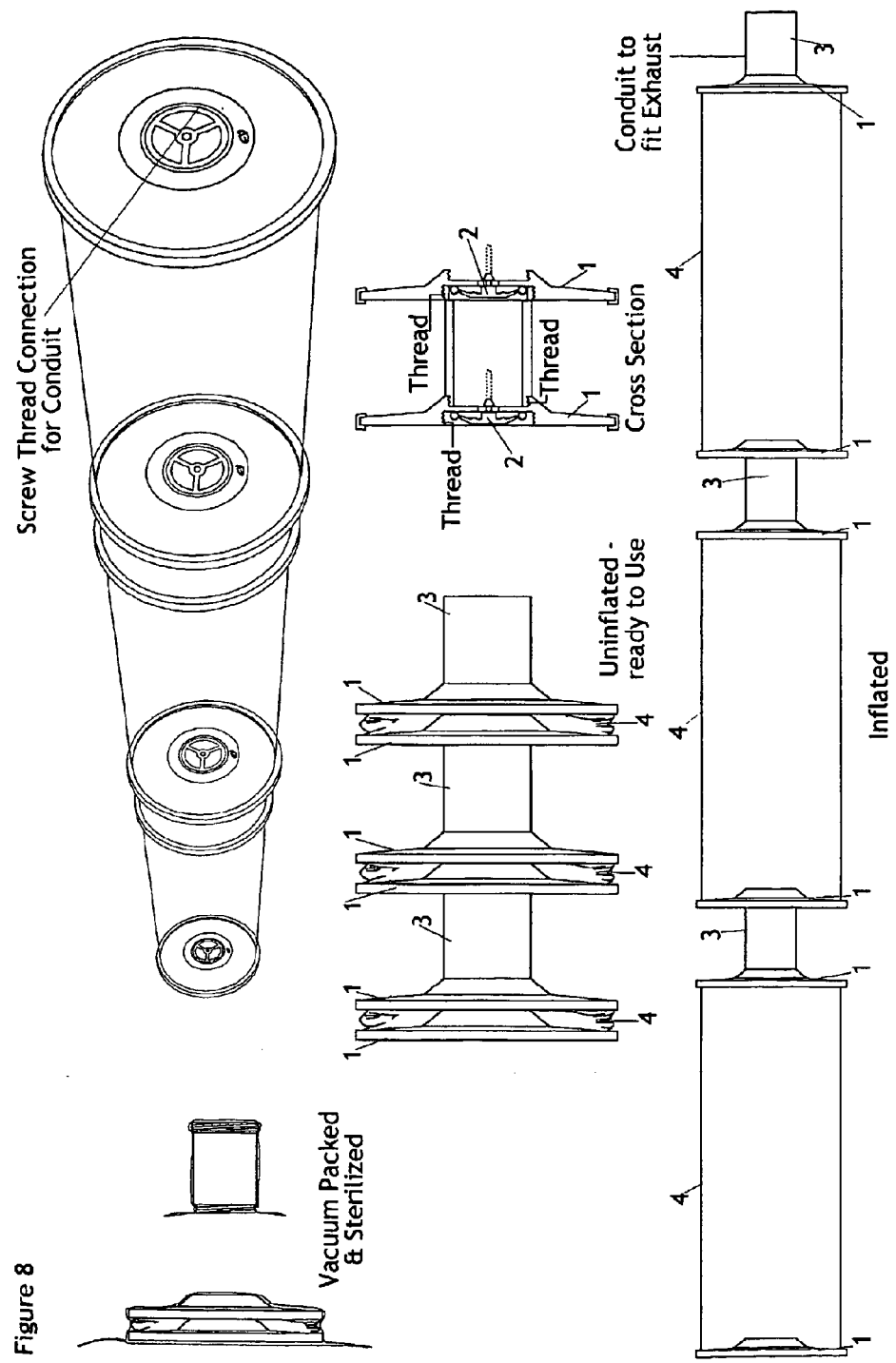

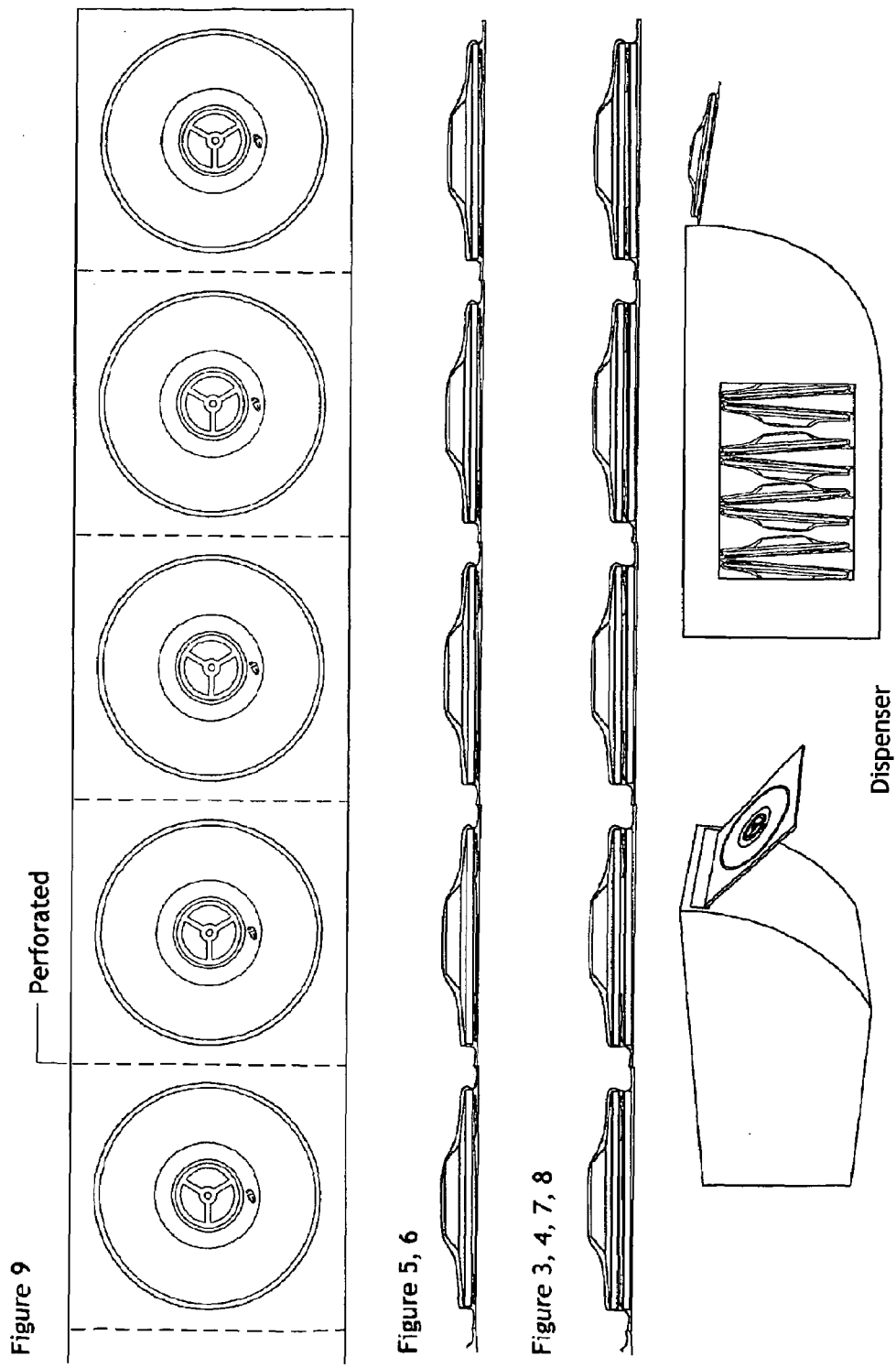

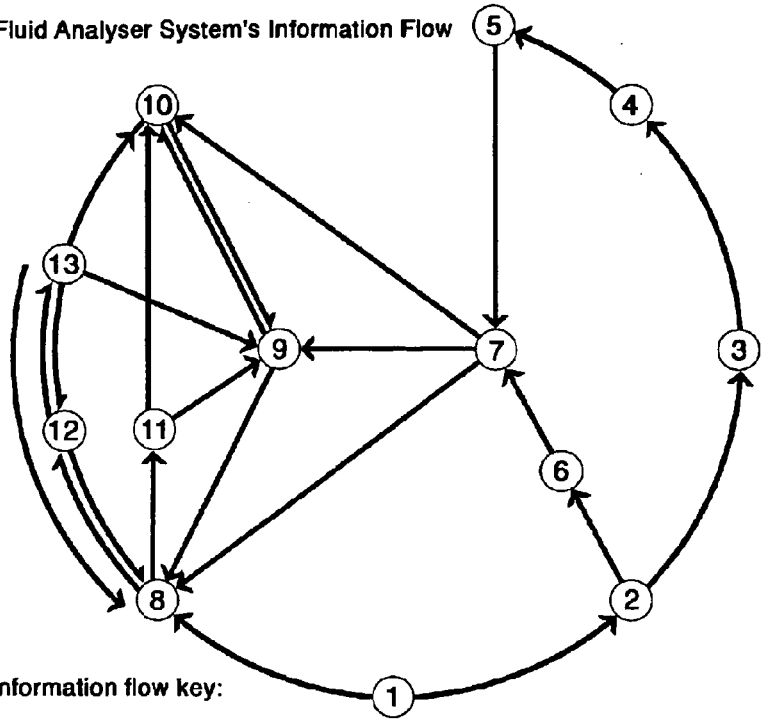

Figure 12. Fluid Analyser System's Information Flow

Figure 12 Information flow key:

1. Remote/ Physical Start-up Digital Re-calibration
2. Start selected test
3. From sensors receive raw data
4. Average/ Magnify data
5. Search fluid database
6. Test Procedural, Tagging and/or Conditions data; Individual, Environmental and/or engine reference data
7. Advisory status report with reference information
8. Store/ Search
9. Comparitive Analysis
10. Print
11. Internal data
12. Remote transfer/ receive
13. External data/ databank

FLUID ANALYSER SYSTEMS

FIELD OF THE INVENTION

The present invention relates to fluid analysers and in particular it relates to improved forms of fluid analysers capable of determining the individual chemical composition of the fluid. In particular the invention relates to analysers which are simple to operate and are both qualitative and quantitative in identification of the components within individual and/or a multitude of fluids. The invention offers a high degree of accuracy without having to change or put additional fluid analyser sensors into the system.

DISCUSSION OF THE BACKGROUND ART

Most analysers rely upon sensors gathering information from within frictional flow rates of fluids. However, the analyser of the present invention works by collecting the fluid sample via a non-invasive methodology. In a preferred embodiment the invention relates to a fluid analyser that is portable and may be used to analyse the samples taken at a remote location and to interact with other fluid analyser systems usually of the same manufacture. Allowing its use in a wide variety of environments and settings.

For the purpose of this document, Fluid means:
i) Consisting of any particles that move freely among themselves.
ii) Particle means, a minute portion of matter.
iii) Matter means, any of numerous subatomic and/or atomic constituents of the physical world that interact with each other.
iv) Constituents means, anything that occupies a space.

Portable fluid analysers are known, the breathalyser used to detect alcohol in a motorist's breath is an example of a portable fluid analyser. Portable, or mobile, analysers are also used for environmental purposes such as the determination of air purity around petrochemical complexes, gas fires and boilers. Portable, or mobile analysers are also used in mining and in other hazardous activities to detect the presence of dangerous fluids.

Existing portable fluid analysers consist of a sampler and an analyser. They do however, suffer from certain disadvantages. Firstly the fluid sampler and the analyser make up a unitary apparatus with operators manning and being required to understand the complexities of the analyser. Furthermore, the results of the analysis cannot usually be compared on the spot with previous data because that is generally stored in a remote location. An additional disadvantage is that typically analysers can usually detect no more than 4 gases in a portable unit at any one time and speciality analysers can usually detect no more than 6 at any one time. The analysers are further limited in that when working on gaseous mixtures they cannot detect a concentration above and/or below a saturation limit which depends upon the nature of the gas.

Existing fluid analysers tend to detect fluids in a flow of fluid in a stream as it passes a detection probe or probes. This technique suffers from the drawback that the probe must be cleaned after each analysis before any subsequent use and it is difficult to get the probe sufficiently clean to prevent contamination for the next test. Also it Is sometimes necessary to recalibrate the probes between each analysis. In many existing fluid analysers each fluid is detected through an electro chemical sensor and the user needs to replace the sensor according to the fluid to be detected. It is then necessary to recalibrate the sensor to detect another fluid.

If the flow rate in one analyser is greater than that of another and the sensors are the same. The device with the greater frictional flow rate should provide a more accurate reading. However to obtain an even greater accuracy and a wider range of fluid analysis, a radioactive scan in a predetermined environment will provide greater accuracy and quantity analysis report.

Chemiluminescence is sometimes used for gas analysis and involves the capturing and interpretation of emitted light during a chemical reaction. Absorption and desorption rates of molecules on surfaces of fluids and their transfer rates from a surface of a fluid are dependent upon temperature. This action is termed surface diffusion and where there is an equilibrium both absorption and desorption occur creating corresponding fluxes of equal magnitude. This type of analyser suffers from the disadvantage that it relies on thermal or chemical reactions induced or otherwise to analyse the intensity values of fluids and thus determine the amounts of fluids that are present.

Gas Chromatography is also used for fluid analysis. This technique separates a mixture of fluids by passing it in solution or suspension through a medium in which the components move at different rates to enable identification of the different components present in the mixture. The fluid analyser system of the present invention however, has no need to pass the sample in the container through a mixture or suspend it in a liquid in order to asses the identity of the contents or their volume within the sample.

It has also been proposed that fluids may be analysed from the reconstructed gas/fluid emissions formed and identified by the addition of chemicals in a calculated manner. The surface relaxation of fluids has the causal effect of emitting a variable light. The variable light from the chemical reaction helps create the environment where electrons invade the x, y and z axis through a process of spilling. Friedel oscillations are created near the surface of fluids which may or may not screen the ions. Where the ions are allowed to withdraw back into the surface of a material the energy received from the material will be reduced or changed. The changes can be used to indicate the nature of the components of the fluid, this process however suffers from the disadvantage that it relies on a chemical reaction.

The refractive index is used to differentiate the light reflected back from different substances thereby providing an identity, however, the light cannot be clearly identified much beyond 6 decimal places which has the disadvantage of categorising different substances under the same refractive index number.

Mass Spectrometry can also be used. The objective of the Mass spectrometry is to separate each mass from the next integer mass and this can be achieved in several ways the first of which is via Unit resolution mass 50 distinguishable from mass 51, for example. The magnetic sector using the Gaussian Triangle peak method of differentiation. The Fourier Transform Ion Cyclotron Resonance (FTICR) system utilises twin peaks with a Lorentzian shape and 10% valley resolution. The Time Of Flight (TOF) mass spectrometer is resolved to a 50% peak-height definition incorporating the Gaussian triangle shape. The two peaks are resolved to a 50% valley.

SUMMARY OF THE INVENTION

Mass Spectrometry is concerned with the separation of matter according to atomic and molecular mass. It is most often used in the analysis of organic compounds of molecular mass up to as high as 200,000 Daltons, (Atomic Mass Unit) and until recent years was largely restricted to relatively volatile compounds. Continuous development and improvement of instrumentation and techniques have made mass spectrometry the most versatile, sensitive and widely used analytical method available today. However, the fluid analyser system of the present invention is capable of a definition of a fluid particle beyond that of a mass spectrometer. Furthermore, the analysis of the present invention utilises captured sample/s where integrity of the sample is maintained. Mass Spectrometry also suffers from the difficulty that integrity is problematic. An additional advantage of the present invention is that the samples can be stored.

In Mass Spectrometry radiation sources, such as lasers, are used, the wavelength of current lasers occurs in approximately the visible wavelengths. Conversion of visible wavelengths into shorter wavelength radiation has many practical applications beyond the intrinsic theoretical interest in production mechanisms, as absorption sources, x-ray heating sources, x-ray lasers. Radiation is amplified through laser energy aimed at the sample. The fluid analyser of the present invention does not require additional energy radiation in order to amplify the signal radiative source of the fluid in the sample container to facilitate the identity of the fluid.

U.S. Pat. Nos. 6,271,522 suggests that spectrometry may be used for gas detection. Similarly U.S. Pat. No. 5,319,199 uses infrared and ultra violet radiation to detect the gases present in vehicle emissions. U.S. Pat. No. 4,746,218 is concerned with spectral absorption to detect and analyse gases. None of those devices enable the simultaneous detection and analysis of a multitude of gases and none of them can detect gases at a low enough concentration to be useful in comprehensive medical diagnosis.

The present invention provides a fluid analyser system, in particular a portable fluid analyser system which overcomes the various disadvantages previously described. The analyser of the present invention does not require probes in the fluid to be analysed and operates on a self contained static fluid sample which thus minimises or avoids contamination of the sample. The analyser of the present invention has the additional benefit that the sample once taken remains sealed to prevent contamination. The fluid analysers of the present invention can be used to develop personal breath profiles which can be stored somewhat like a fingerprint and the stored profile can be checked against a new sample taken at a later date or during health checks.

According to the present invention detection of the radiation emitted by the various components in a sample of the fluid is used to determine the nature of and quantities of materials present in the fluid. This provides the option that only the radiation emitted by the molecules in the sample can be used for analysis and additional sources of energy, such as light, heat, sound and vibration may not be required.

Accordingly in one embodiment the present invention provides a fluid analyser system comprising a receptacle(s) for the collection of a fluid sample and an analysis apparatus containing a consistent light condition compartment containing temperature detection device(s) into which the receptacle containing the fluid sample may be placed and means for detecting the radiation emitted by the sample, together with means for magnification of the detected signal.

The present invention further provides means for translating the magnified signal into the nature and quantity of the fluids present in the sample said means being referenced according to:
a) the known volume of the inflated receptacle
b) the light condition of the fluid sample
c) the temperature of the fluid sample
d) the duration of the radiation scan and/or
e) the distance of the radiation scan.

The present invention further provides a fluid analyser system comprising:
i) A receptacle for a fluid sample.
ii) A consistent light condition environment in which the receptacle can be placed.
iii) A timing device for measuring duration of the scan of the radiation emitted by the fluid sample in the receptacle.
iv) A temperature sensor for determining the temperature of the sample.
v) Detector(s) for receiving data from the radiation emitted by the sample located at a predetermined distance from the sample.
vi) Means for translating and magnifying the signal from the detector(s) enabling identification of the intensities and the peak intensity values' wavelengths.

Optionally the system may also include a light meter for determining the consistent light condition environment.

The peak intensities and peak intensity values may then be summed and/or correlated with either known/unknown peak intensities and/or peak intensities values (nm wavelength values) to indicate the nature of the fluids present in the sample and to determine the concentrations of the fluids in the sample.

The detector(s) used in the present invention is preferably a radiation absorbance device(s) which receives the radiation levels according to the nano metre wave energy received from fluid(s) within the sample of fluid as recorded over a predetermined time span via a divided amalgam-coated glass or other appropriate material surface. The surface records the radiation levels received at the specific nano meter wave divided cells. These cells are convenient indicators used for the purpose of identification of the sample fluid and its intensity volume.

This system may operate via a specially designed, fully coordinated, computer driven software system to provide an advisory status report of the content of the fluid and the conditions under which the test was performed.

The analyser system of the present invention preferably also includes a means for the measurement of the humidity and dew point of the sample and also means for determining the atmospheric pressure. These measurements can be stored to enable these factors to be taken into account if and when the profile is compared with another sample or for reference purposes. This may be the case when the analyser is used for fluid/emission analysis for health and environmental purposes. In a further preferred embodiment the system is provided with a GPS so that the date, time and location (altitude, longitude and latitude) of the position where the sample was taken can be recorded.

The system preferably also includes a means for the measurement of gravity, sound and vibration, velocity and direction.

The analysers of the present invention can detect the presence of a multitude of fluids in a sample and they can also detect the presence of the amounts of fluids present as low as parts per billion and lower. The fluid analyser of the present invention has the benefit that it may be used at anytime by trained operators in most environments and conditions. Furthermore, the analyser system is versatile. For example, the sample may be taken at one location and the scanning and analysis system may be used in the same or another location. The detection signal, either via a remote control or operator, may then be transferred to another location for magnification, analysis and/or storage or kept in the same location for magnification, analysis and/or storage. Data may also be received in the same manner and this data and any other stored data may be used for comparative purposes being checked against any previous or current internal and/or external test results. If the data analysis system is at a different location from the sample taken, it is preferable to install relevant reference data into the fluid analyser system including the time, conditions and location of where the sample was taken. Maintaining the integrity of the reference data.

The techniques of the present invention may be used in an industrial environment for the detection of gases in particular pollutants and toxic gases in for example mines, chemical plant, oil rigs, oil wells and the like. It may also be used in the evaluation of engine combustion, the emissions generated and their interaction with the environment. It is particularly useful in the detection of particulates. This is useful in the monitoring of engine performance, which is becoming increasingly important as environmental legislation becomes more severe. This is particularly relevant to diesel engine performance. The techniques may also be used for, but not limited to, environmental studies where atmospheric changes are significant such as in weather forecasting and forecasting, volcanic eruption and earthquakes. Additionally, the analysers can be used to detect different gases or combinations of gases that plant life can produce prior to earthquakes.

A particular use of the techniques of the present invention is in the detection of the content of human and animal breath. The techniques therefore may be used in the production of data for the monitoring of human health. In addition, the ability to take and scan samples in one location, such as in the home, in an ambulance or at an accident site and transmit the results to, for example, a doctor's surgery or a hospital for analysis and the production of results can enable more rapid diagnosis and treatment.

In whatever environment the present invention is used in order to determine the identity and volume, a sample of the fluid to be analysed is first collected in a receptacle(s). In order to get a sharp image of the radiation emitted by the sample the walls of the receptacle should have a high optical clarity. The side walls of the receptacle should be flexible but not elastic. The receptacle is preferably provided with a one-way valve to enable it to be filled through the one-way valve. The valve will prevent escape of the introduced fluid and ensures that the receptacle is automatically closed when it is full. The receptacle should be such that there is minimum contamination. The size and the shape of the receptacle is not important and will depend upon the environment in which the analyser is used.

The materials used to make the receptacle should have minimal absorption and dispersion rates and withstand potentially very high temperatures. The walls of the receptacle are preferably thin to improve the optical clarity and the accuracy of the fluid sample temperature.

The degree of optical clarity required will depend upon the use to which the receptacle is to be put. However, when used for fluid analysis high clarity is required as indicated by the transmission of a high percentage of ultra violet and visible light. A solar transmission, as determined by ASTM E-424, greater than 90% preferably greater than 95% is preferred. For this reason fluorocarbon films such as FEP available from Du Pont is a preferred material for the production of receptacles especially those to be used in gas analysis. Use of FEP and like materials has the added benefit that it cannot be compressed.

The walls of the vessel should also be flexible and inelastic. Flexibility means that the material at its thickness of use is able to completely recover its original shape and form from compression, concertina, flat pack, fanfold, stack, bend or twist. This comprehensive flexibility simultaneously maintaining the integrity of their contents within a high optical clarity material.

In one embodiment rigidity may be imparted to part of the structure through the incorporation of a rigid moulded part such as the top and/or the base of the receptacle. The integrity of the contents is still maintained as aforementioned, however the optical clarity is sacrificed at top and bottom of the receptacle in favour of rigidity and strength.

The receptacle is conveniently made by mass produced methods and we have found that fluorocarbons such as FEP (polytetrafluoroethylene), preferably virgin FEP, supplied by Du Pont, MFA Ausimont and PFA are particularly useful materials from which the sample bag can be made. Conveniently the receptacle is made in five pieces, the sample bag itself, the non-return valve, the non-return valve holder, a tamperproof clip and a fluid delivery tube such as a mouthpiece. For the receptacle which provides a firm fit for the consistent light environment chamber in FIG. 13, the bag is preferably extruded and sealed at one end by a welding technique (see FIG. 5). The bag is provided with an opening into which the valve holder and valve can be sealed and clipped. The valve holder may also be injection moulded as can the valve and fluid delivery tube from materials such as medical grade polypropylene, as can the base for such receptacles as shown in FIGS. 3 and 4. A vacuum is created within the receptacle, then sterilised and vacuum packed to avoid contamination prior to use. Two or more receptacles may be linked in series to allow parallel analysis of more than one sample.

The valve holder is preferably shaped so that a fluid delivery tube, such as a mouthpiece can be readily attached to the top of the receptacle.

The shape of the inflated receptacle should be such that it is a firm fit within the consistent light condition environment of the fluid analyser system. We prefer that the receptacle, upon inflation by the fluid to be analysed is cylindrical at the point where the radiation detectors are positioned. The valve and the materials from which the container is made should be such that the container cannot be expanded beyond its original capacity due to inflation by the pressure of the sample.

At the time of collection of the sample of the fluid to be analysed it is preferable that the temperature of the sample should be measured and recorded together with other significant information such as the humidity, atmospheric pressure and location.

At the time when the fluid sample in the receptacle is to be analysed by the fluid analyser, it is also preferable to determine the temperature of the fluid sample. A mechanism is preferably provided for a temperature probe to be inserted through a wall of the consistent light environment chamber to touch the skin of the sample bag contained within the consistent light environment. The probe without penetrating the skin makes contact with the sample bag. Due to the flexible nature of the sample bag, the wall of the bag can surround the temperature probe encasing the tip and the fluid analyser system can then start taking measurements. The mechanism driving the temperature probe is controlled by variable resistance ensuring for each time the probe is positioned it will be encased by the bag but penetration is prevented. Measurements of the ambient temperature of the consistent light environment chamber can also be taken and recorded. The light environment chamber is preferably made of a single material to reduce radiation contamination. It should be opaque and polypropylene is a suitable material. It is preferred that no resins or adhesives be used in the manufacture of the light environment chamber.

The duration of the scan is pre-determined. The measurement of duration is the receiving device(s)'s allowable exposure time to the radiation source (fluid sample). From start to finish the time increment can vary according to the user's requirements typically ranging from but not limited to milliseconds up to 7 seconds and beyond. As previously mentioned it is preferred to use Charge Coupled Device (CCD) detectors to register the radiation emitted by the sample.

Further arrangements may also be made for the determination of the humidity and thereby the dew point. It is however important that the sensors do not penetrate the skin of the container so that there is no physical interference with the fluid sample.

In the preferred operation of the present invention once inflated with the sample of the fluid to be analysed the receptacle is placed into the consistent light condition, preferably dark environment compartment next to a detector which is preferably a Radiation Absorbance Device(s) (RAD). The compartment should then be closed so that normal light will not interfere with the analysis of the fluids. The light reading in the compartment can then be measured and recorded. The process variables such as temperature, pressure and humidity are then measured and recorded. The Radiation Absorbance Device(s) (RAD) then take a measurement of the various radiations emitted by the sample over a pre-determined period of time. To determine the presence and quantity of pre-selected individual fluids, the analyser system having magnified the data of the scan, matches and analyses the wavelengths specifically concerned and their peak intensities against known data already stored in the fluid data base. Alternatively, the preferred method of detecting fluids that are unknown at the time of sampling is to utilise the full range of the Radiation Absorbance Device(s) (RAD), whether sub-infra sonics, infra sonics, sonics, ultra sonics, microwaves, infra red, ultra violet, x-ray, gamma, cosmic and ultra-cosmic. In the preferred operation the process variables such as temperature, pressure and humidity are then measured and recorded again. The fluid analyser system software can then not only determine the fluids present in the sample through a databank of the known wavelengths of fluids, but can also compute the amounts of each identified fluid present through the measurement of the fluid intensities.

The data that is collected by the analyser is preferably magnified using standard curve fitting and signal magnification techniques which can incorporate multiplication and spectral splitting of the pixels. The magnified signal may then be used to identify the fluids present in the sample via the software. This is achieved by comparison against a stored information bank of known wavelengths of fluids. Each molecule of a differing nature will have differing levels of resonance or wavelengths. The system preferably uses software that can sum the absorbances at each of the particular values during or after the radiation measurement, to give the quantity present of each of the fluids which have been identified, within the spectral range (nm) of the Charge-Coupled Device (CCD) detectors being used within the RADs. Knowing the volume of the inflated receptacle used, the fluids are expressed as a percentage of the sample(s). The accuracy of the measurement may be increased by taking multiple measurements of one or more samples.

All fluids at the time of sampling will be analysed under the same conditions. Even though each sample's process variables such as temperature or pressure may differ. The intensity values recorded will be in proportion at the time. The individual values of intensity are not as important as the relationship they have as a portion of the whole. Therefore, if temperature changed, the registered intensity values throughout the spectra analysed will change accordingly at the time. Consequently, the volumes identified will be in accordance to the process variables at the time and location of sampling. The temperature variance is important as changes to the registered and non-registered intensity values are not linear when expansion and retraction occur.

Having been able to identify the fluids present with their volumes expressed as a percentage of the sample, many characteristics of the fluids, such as weights and sizes can be determined. This will help construct a far more comprehensive picture and moving model of fluids and their real time activities.

BRIEF DESCRIPTION OF THE DRAWINGS

The invention is illustrated by the accompanying drawings in which

FIG. 1 is a schematic flow diagram of the performance of the system of the present invention.

FIG. 3 shows the cylindrical shaped receptacle to be used for collection of a sample to be analysed in uninflated form.

FIG. 4 shows the cylindrical shaped receptacle in inflated form.

FIG. 5 shows the receptacle to be used for collection of the sample to be analysed by the consistent light environment chamber shown in FIG. 13.

FIG. 6 shows a receptacle with a flexible base which can be used, on inflation, in an appropriately shaped consistent light environment chamber for analysis of a fluid sample.

FIG. 7 shows a receptacle which can collect a fluid sample. The valve holders and valves are positioned at either end of the extruded bag enabling the fluid emission to pass through the now inflated receptacle and at any given point in time, a sample can be collected of the fluid emission.

FIG. 8 illustrates how several receptacles such as those illustrated in FIG. 7 may be used in series to enable parallel analysis of more than one sample.

FIG. 9 illustrates how receptacles described in FIGS. 3, 4, 5, 6, 7 and 8 can be distributed and dispensed individually by tearing/breaking the perforation. The conduit of any description may then be attached.

FIG. 12 is a flow chart of an information flow during an analysis performed according to the present invention.

DETAILED DESCRIPTION OF THE PREFERRED EMBODIMENT

As shown in FIG. 1 a test is performed by starting up the equipment selecting the test type and collecting a sample of the fluid to be analysed in the receptacle. The test is then started and the temperature and optimally the humidity/dew point and atmospheric pressure are determined. The radiation detector(s) are then activated and a measurement of the radiation emitted by the fluid sample is taken over a pre-determined duration and recorded. According to the nature of the test several samples may be analysed or the sample may be subjected to several measurements. As FIG. 1 also shows the data storage allows for the capture of a wide range of additional data appropriate to the nature of the sample. For example if the analysis is of breath, perhaps for medical purposes, then the location (at work, at home, travelling etc) can be recorded as can (indoors, outdoors, underground). Similarly the climatic conditions can be recorded as can the exact date, time and location at which the sample was taken.

As shown in FIG. 1, the user/controller has the ability to install data into the fluid analyser system's database by means of downloading information, installing from a disc, and/or a user/controller inputting data. In addition each test result can be stored and may be automatically tagged by the user's title of the test, date, time and GPS location. The test is preferably, but not necessarily, stored chronologically and externally either in a bank of information, FIG. 1, and/or a media format with the test tag stored internally on the fluid analyser storage database, also chronologically, for immediate access to the result externally, if agreed by all concerned. This process can be reversed if the end user so chooses alternatively data can be freely extracted to suit.

Preferably, the present invention also makes provision for smart card access and deny ability as shown in FIG. 1. That is a securing methodology for information considered confidential.

Figure 2B:
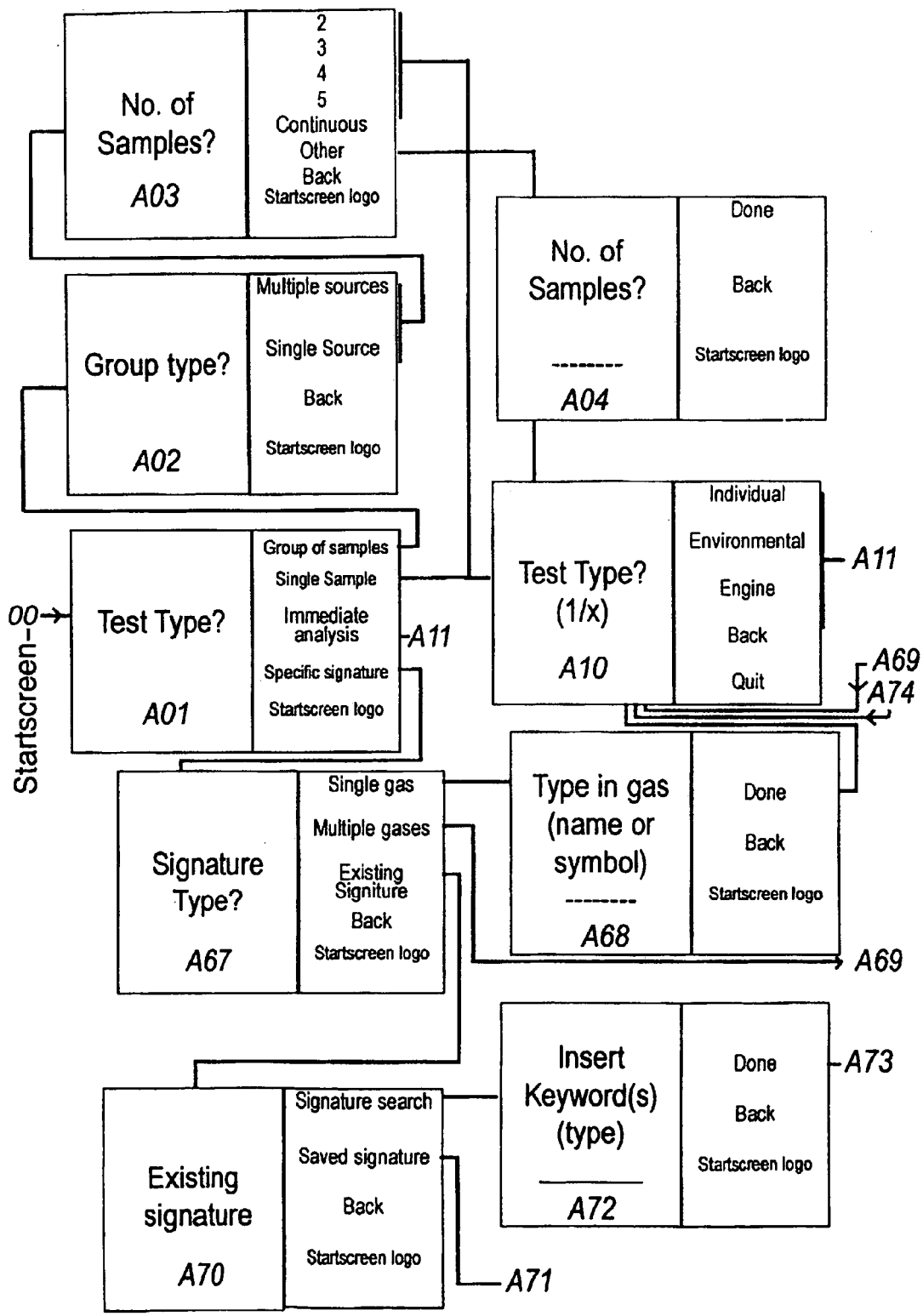
FIG. 2 illustrates how the invention can be used as a health diary.
FIGS. 2a through 2v illustrate how the invention can be used as a health diary.
Figure 2C:
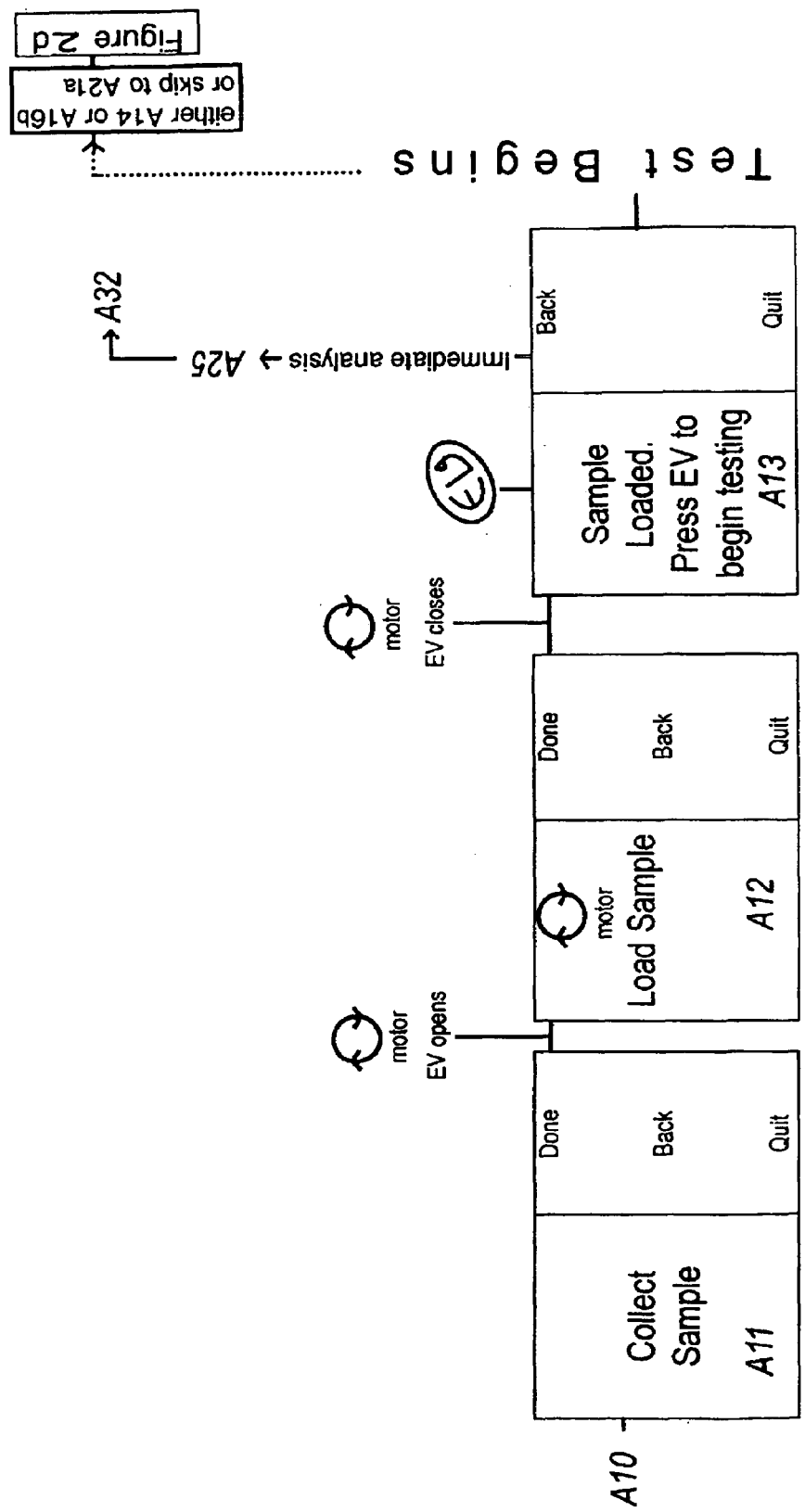
Figure 2D:
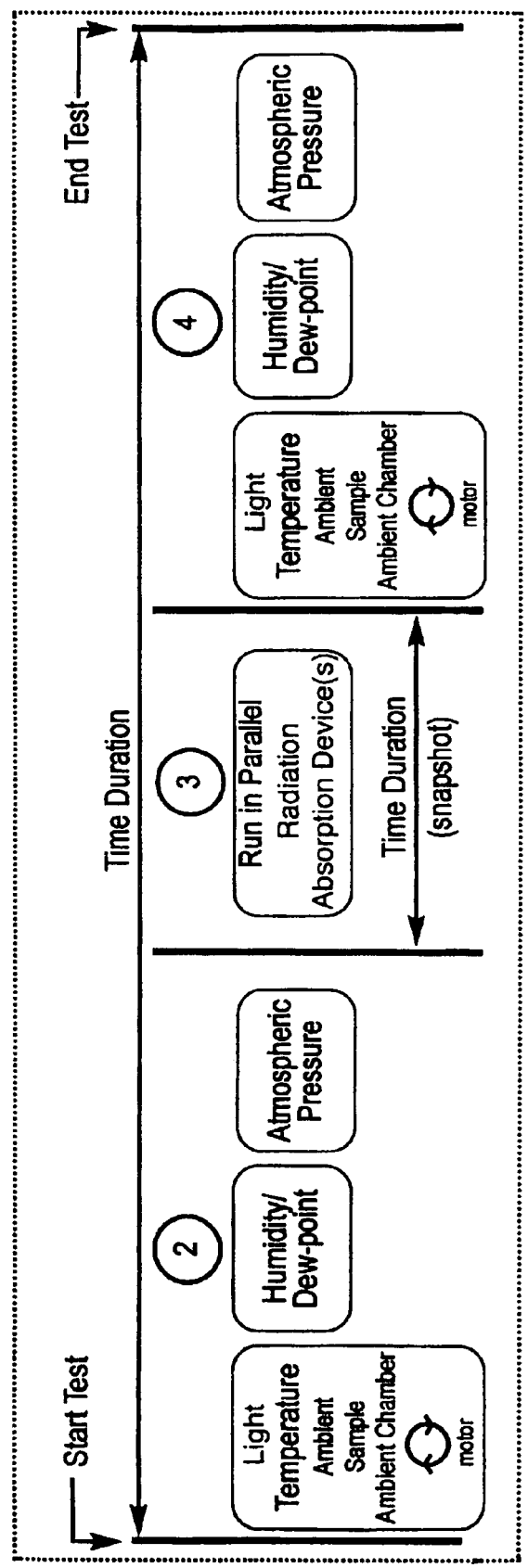
Figure 2E:
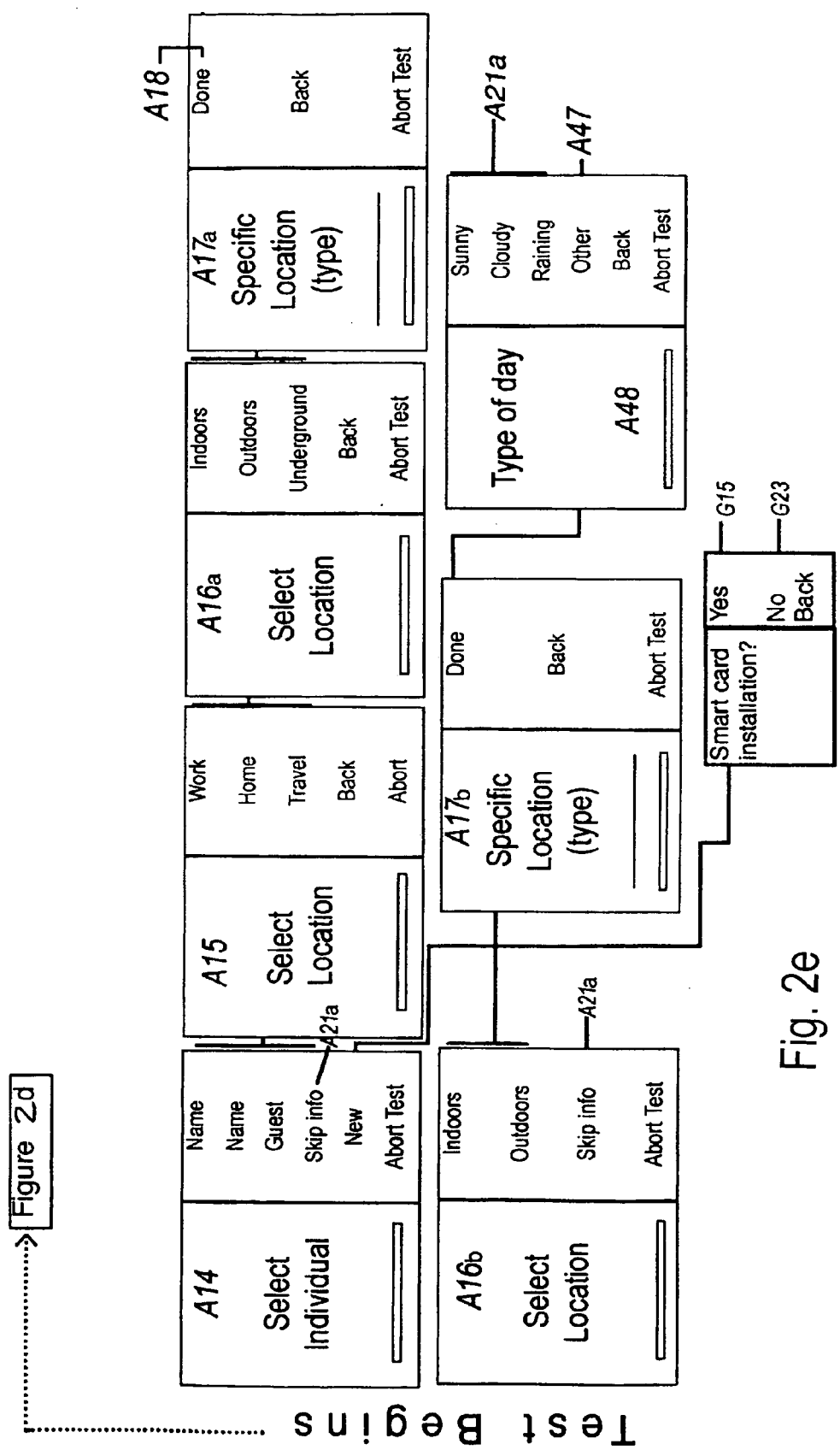
Figure 2F:
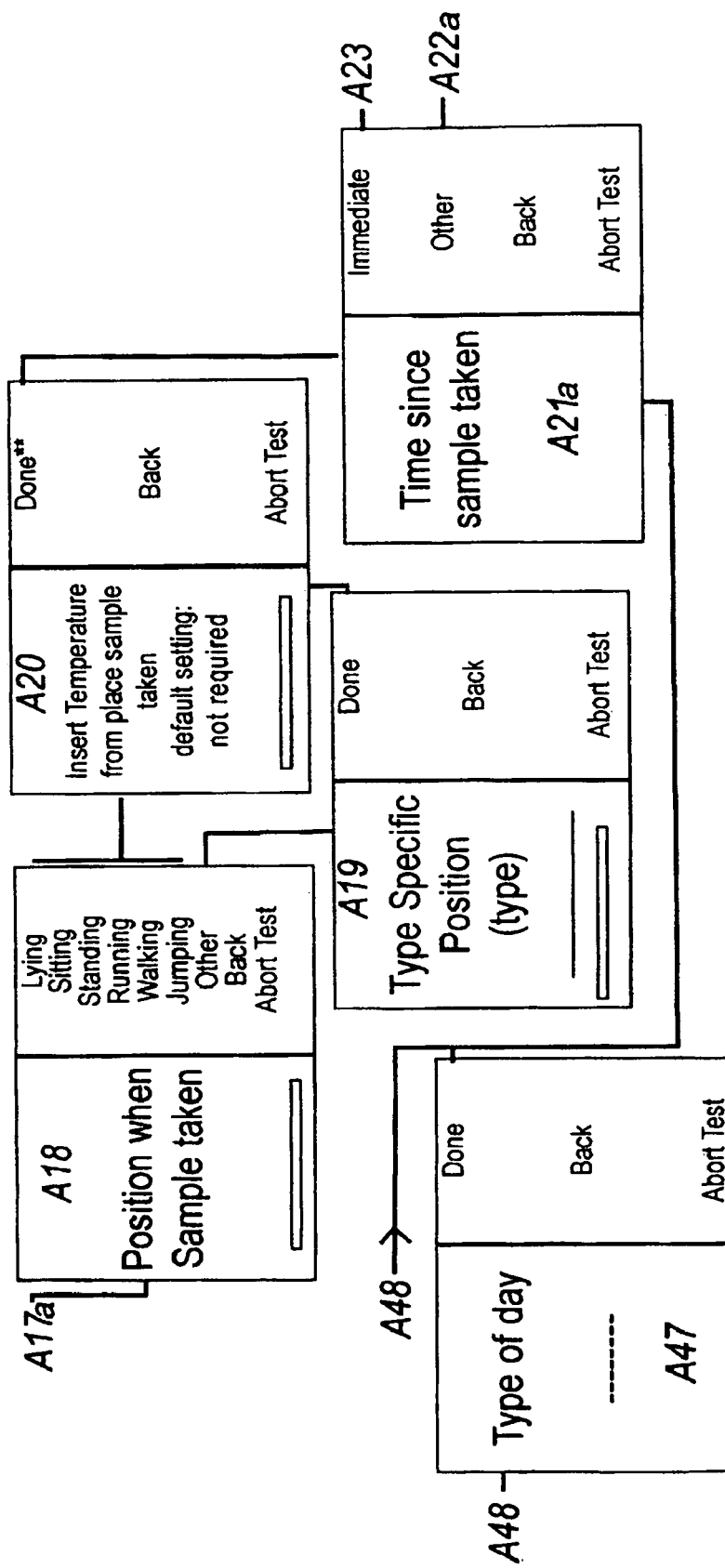
Figure 2G:
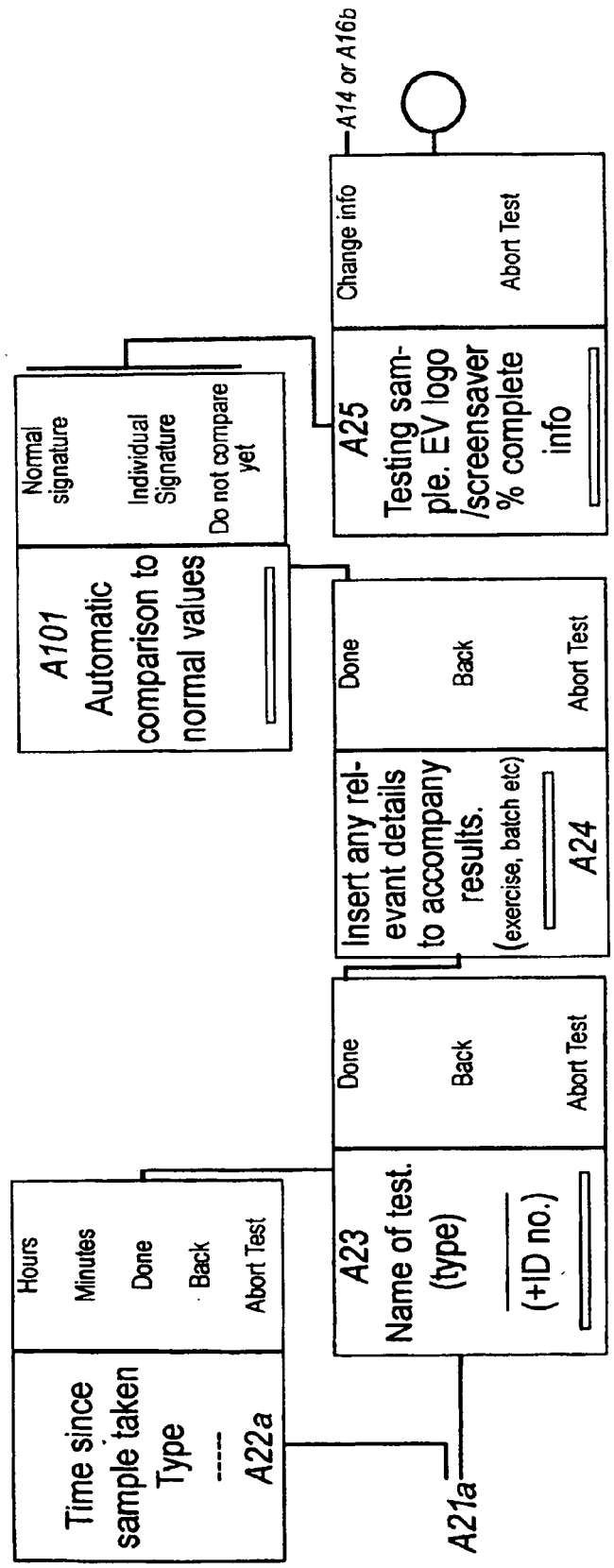
Figure 2H:
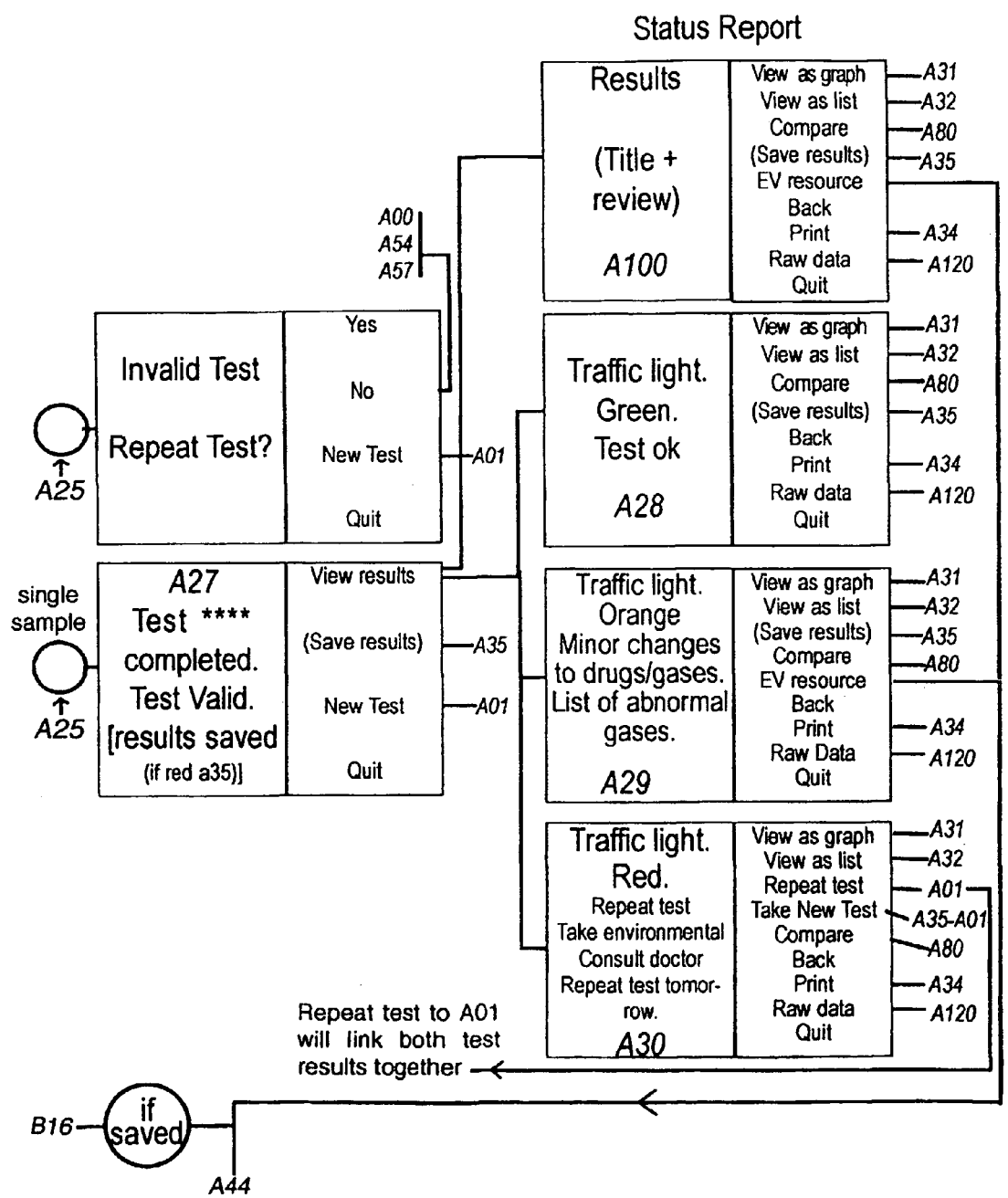
Figure 2I:
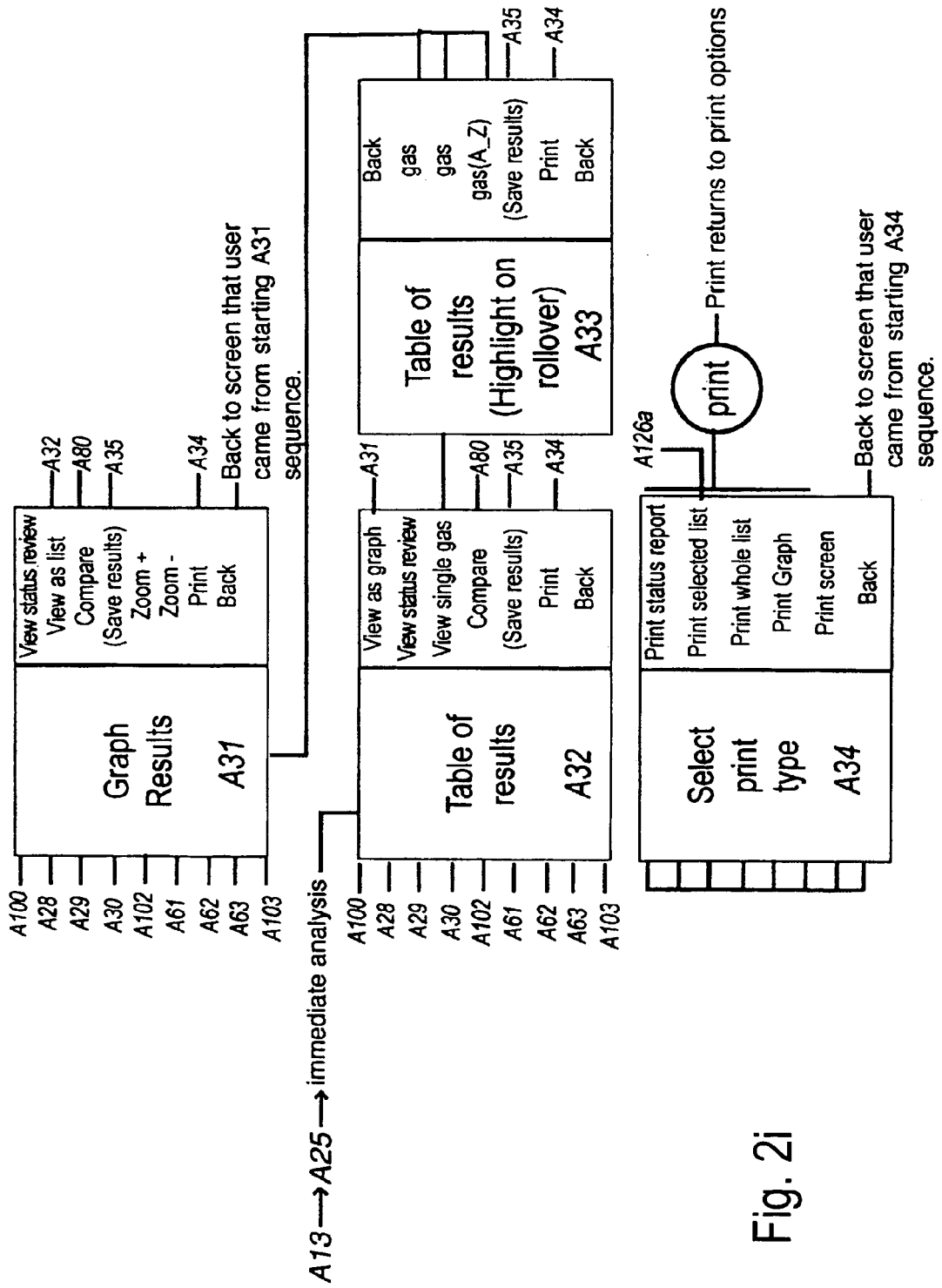
Figure 2J:
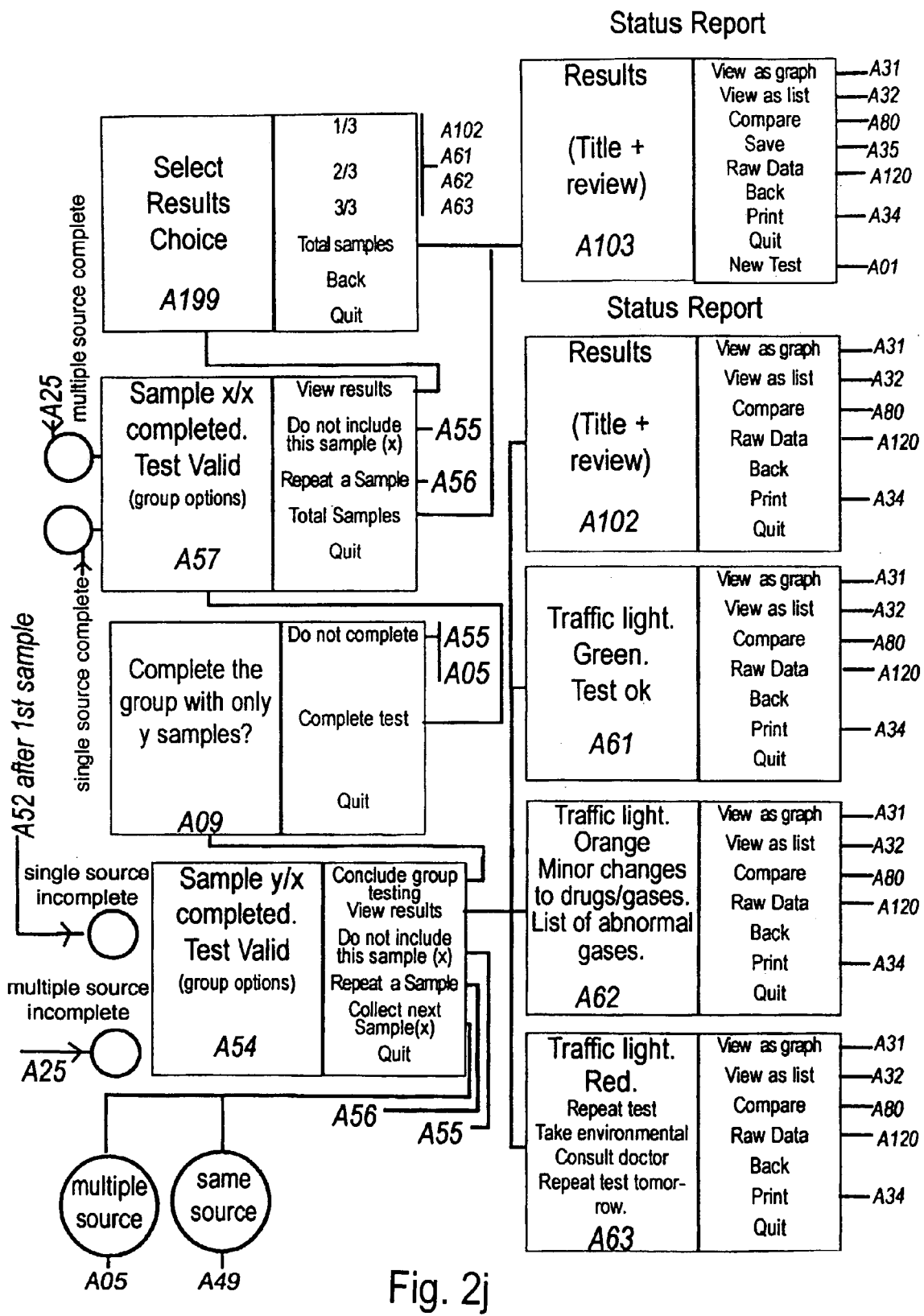
Figure 2K:
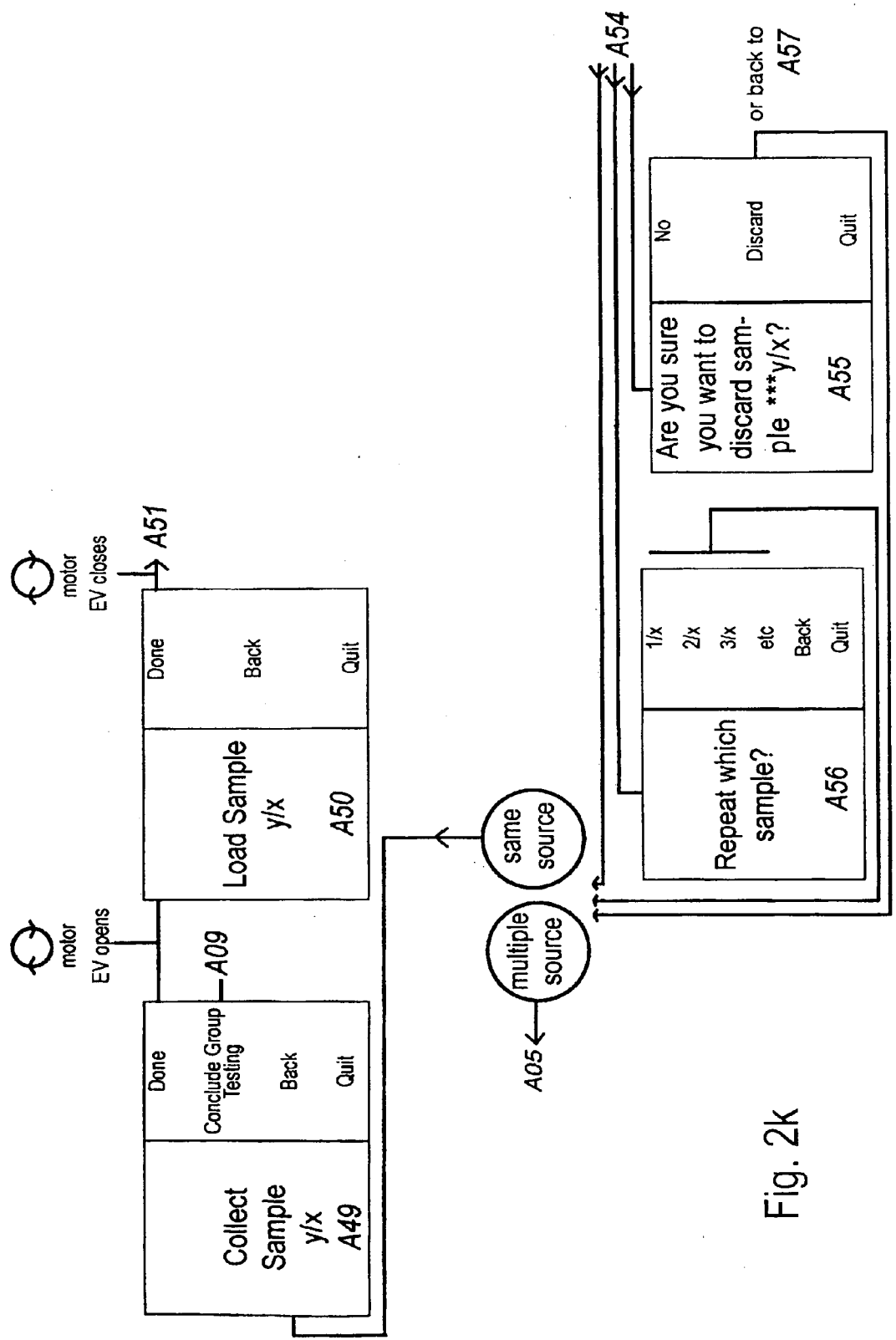
Figure 21:
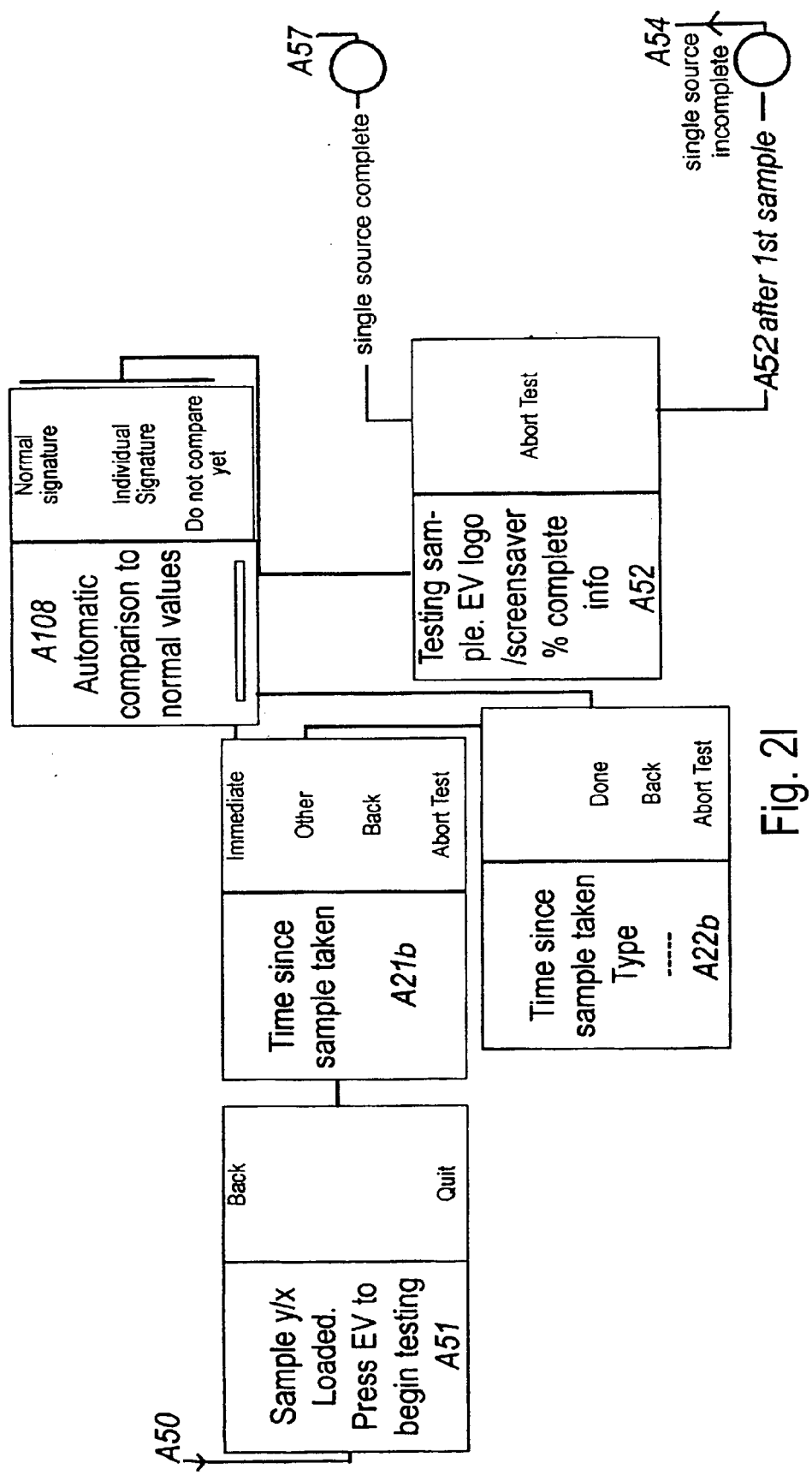
Figure 2M:
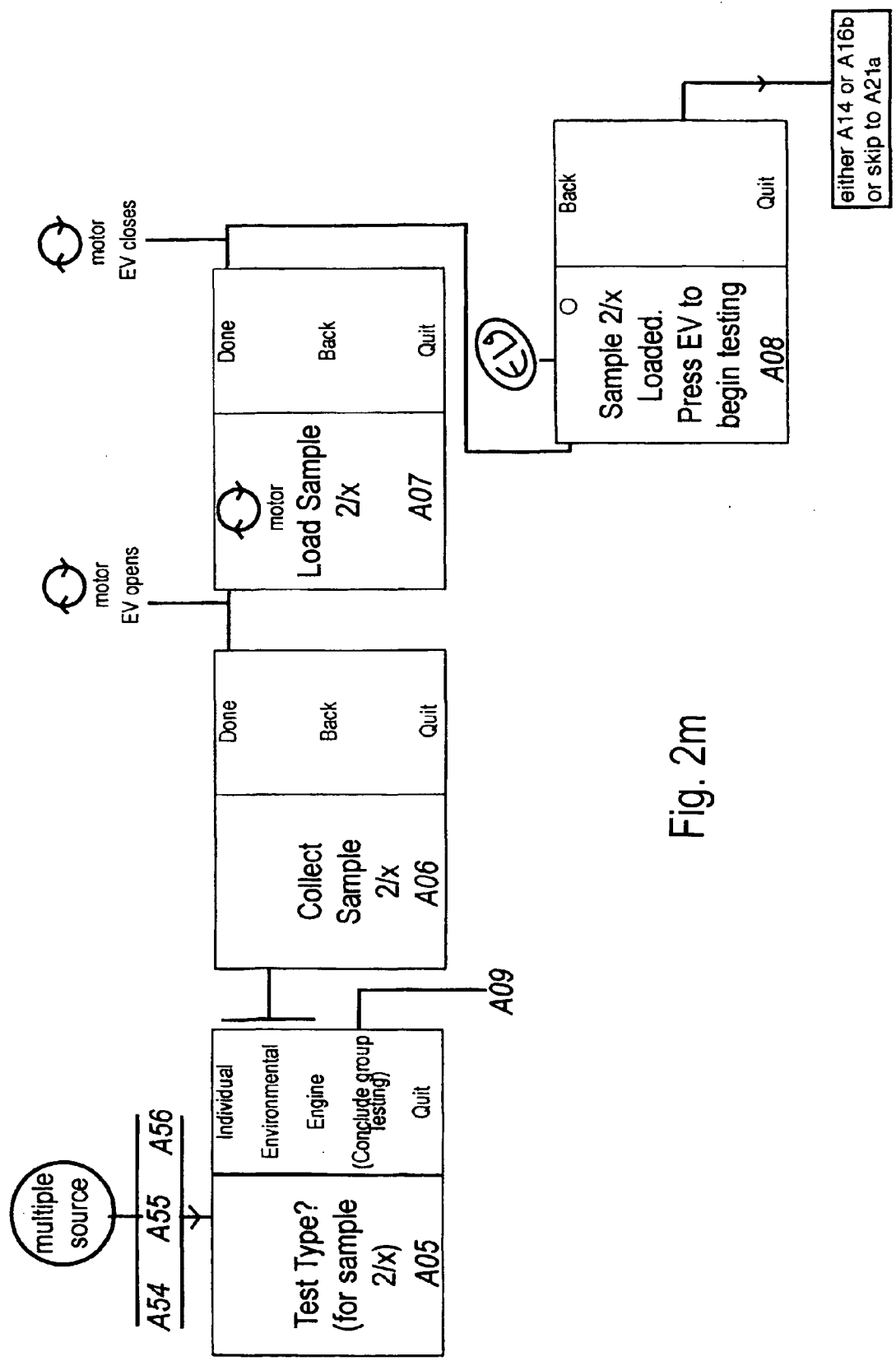
Figure 2N:
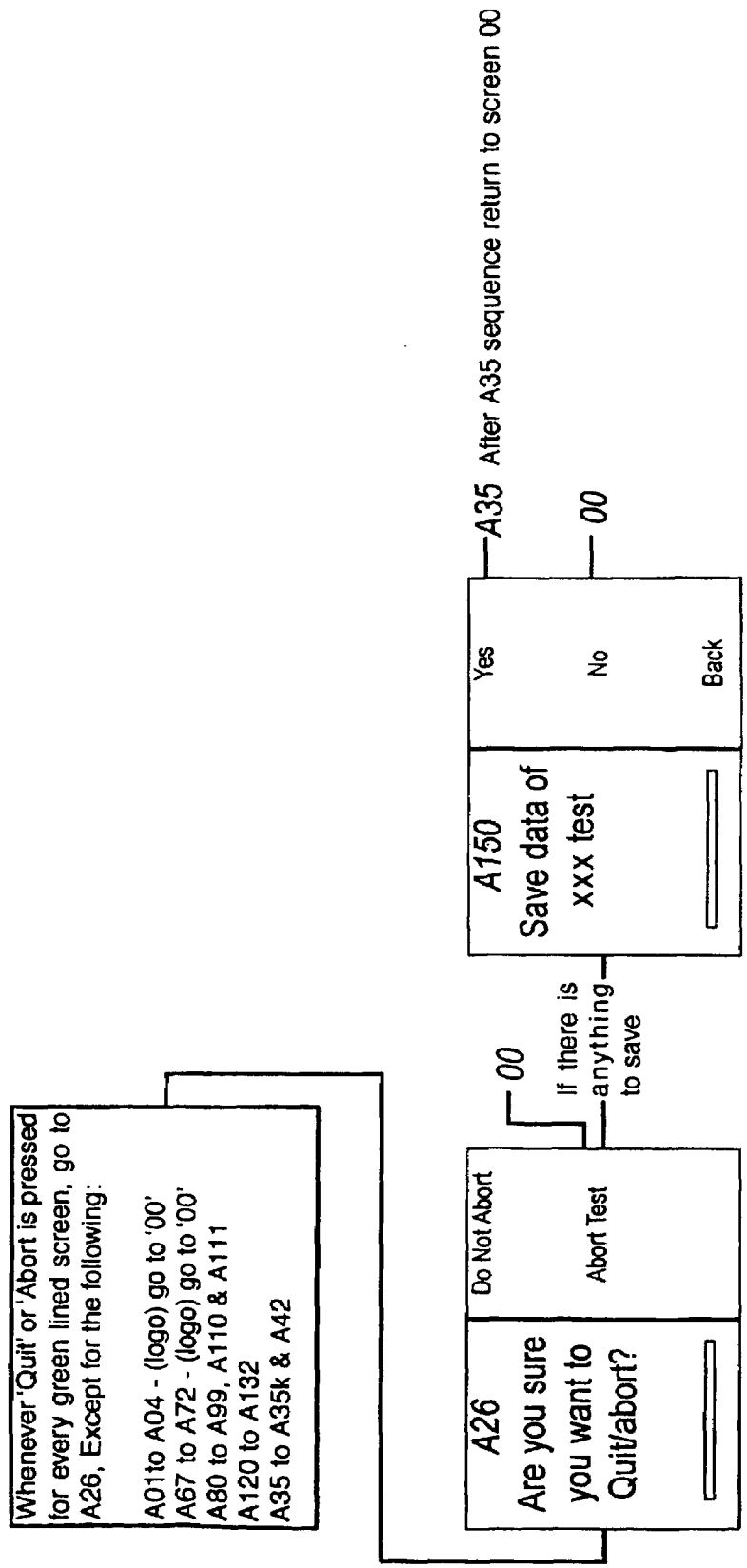
Figure 20:
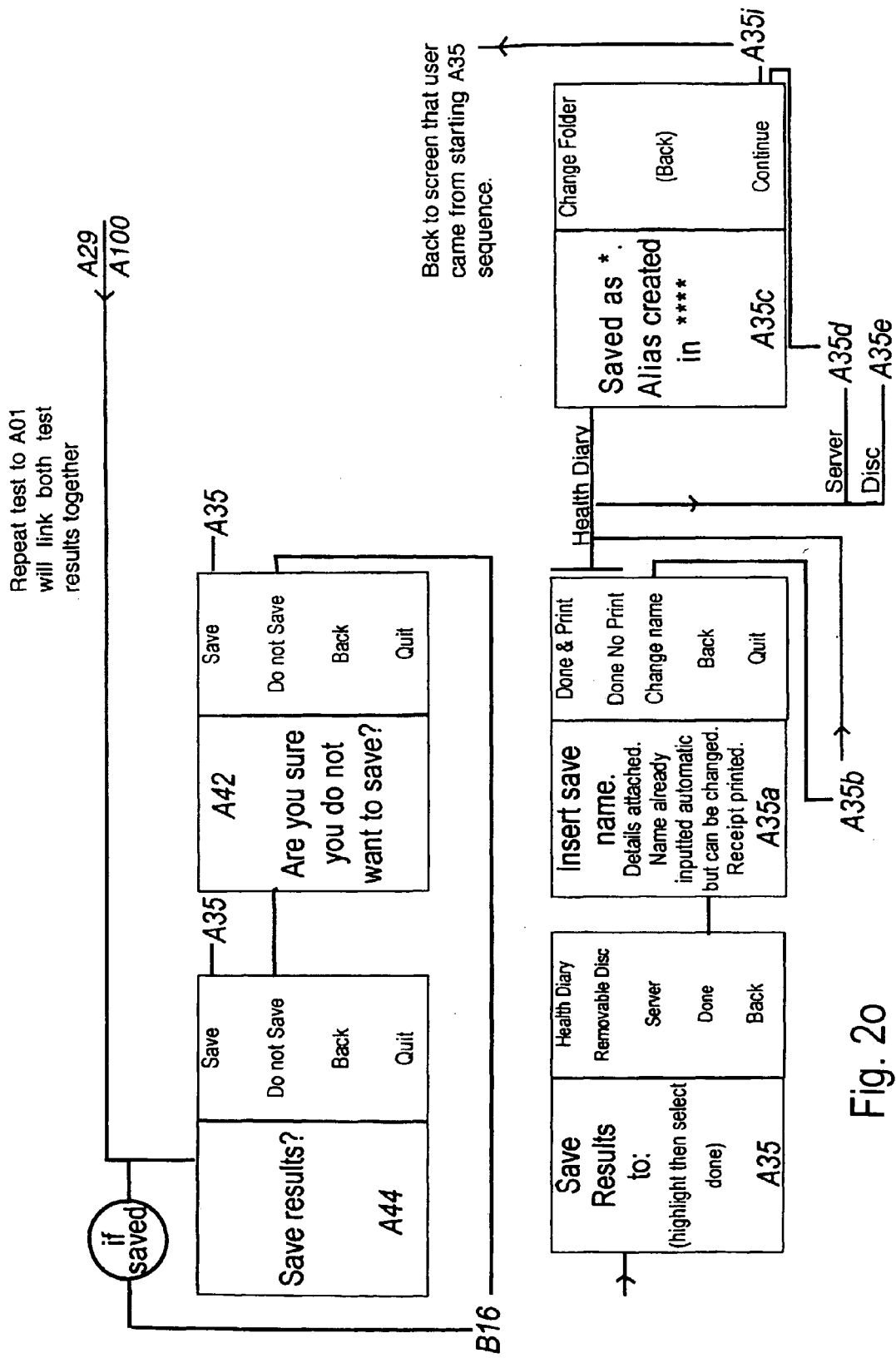
Figure 2P:
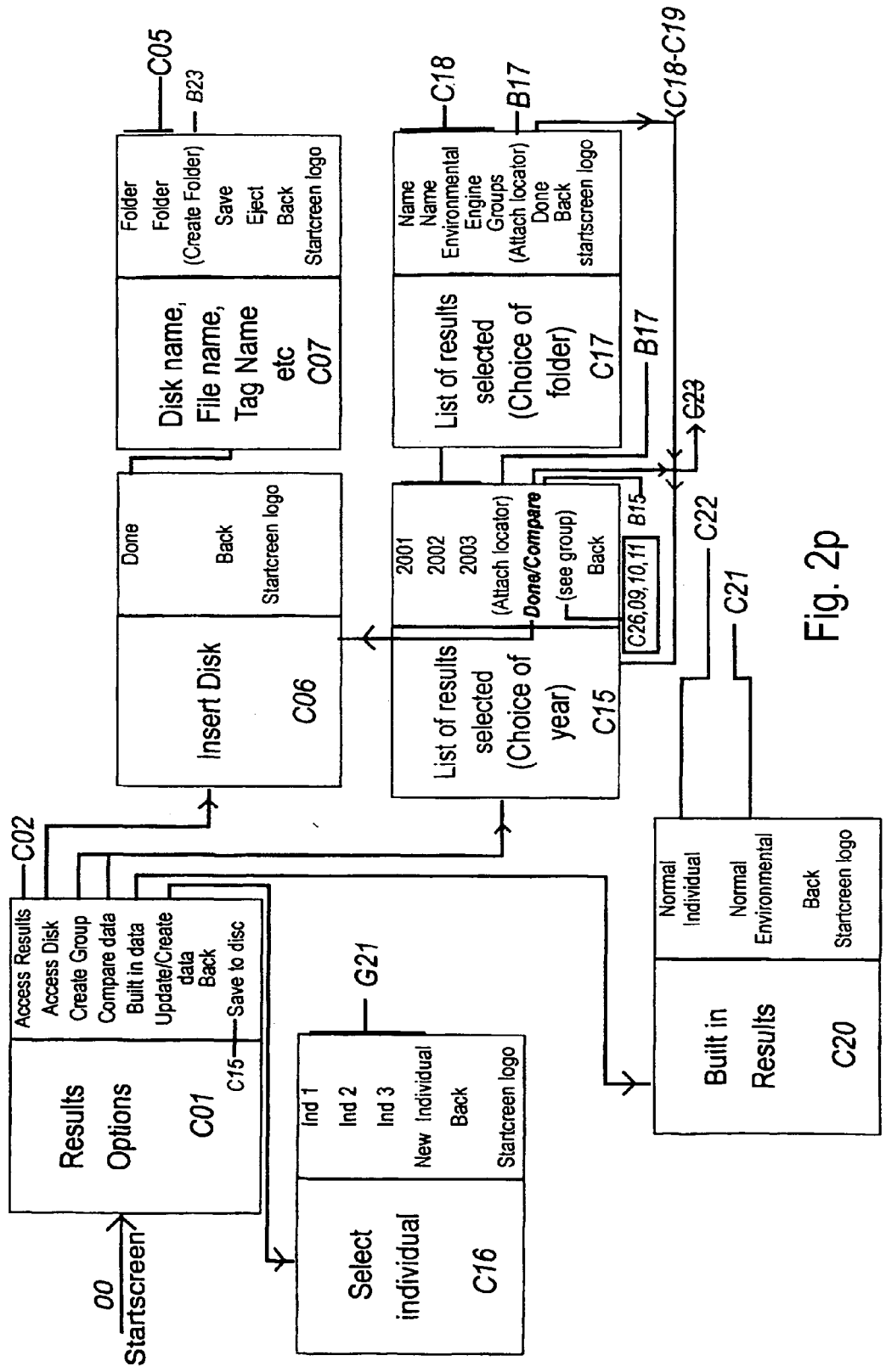
Figure 2Q:
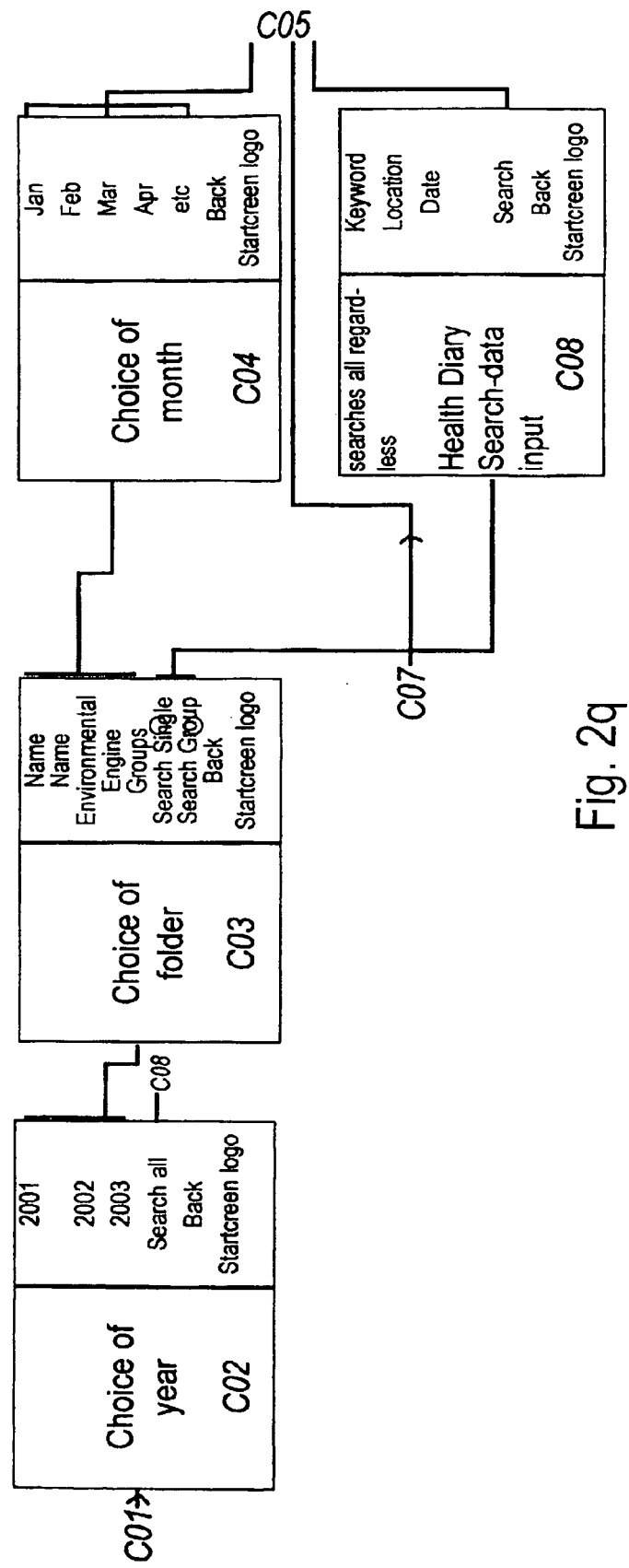
Figure 2R:
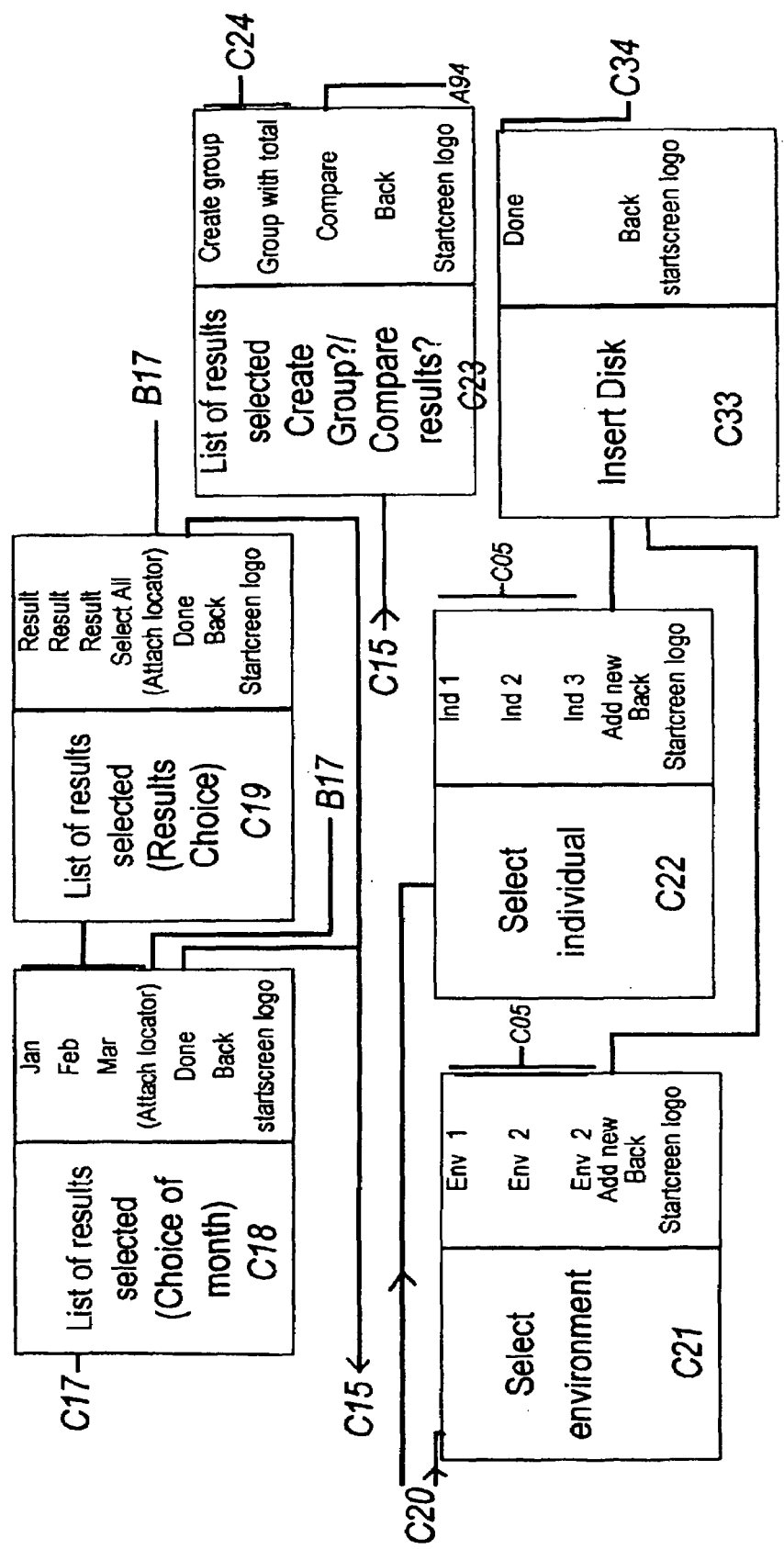
Figure 2S:
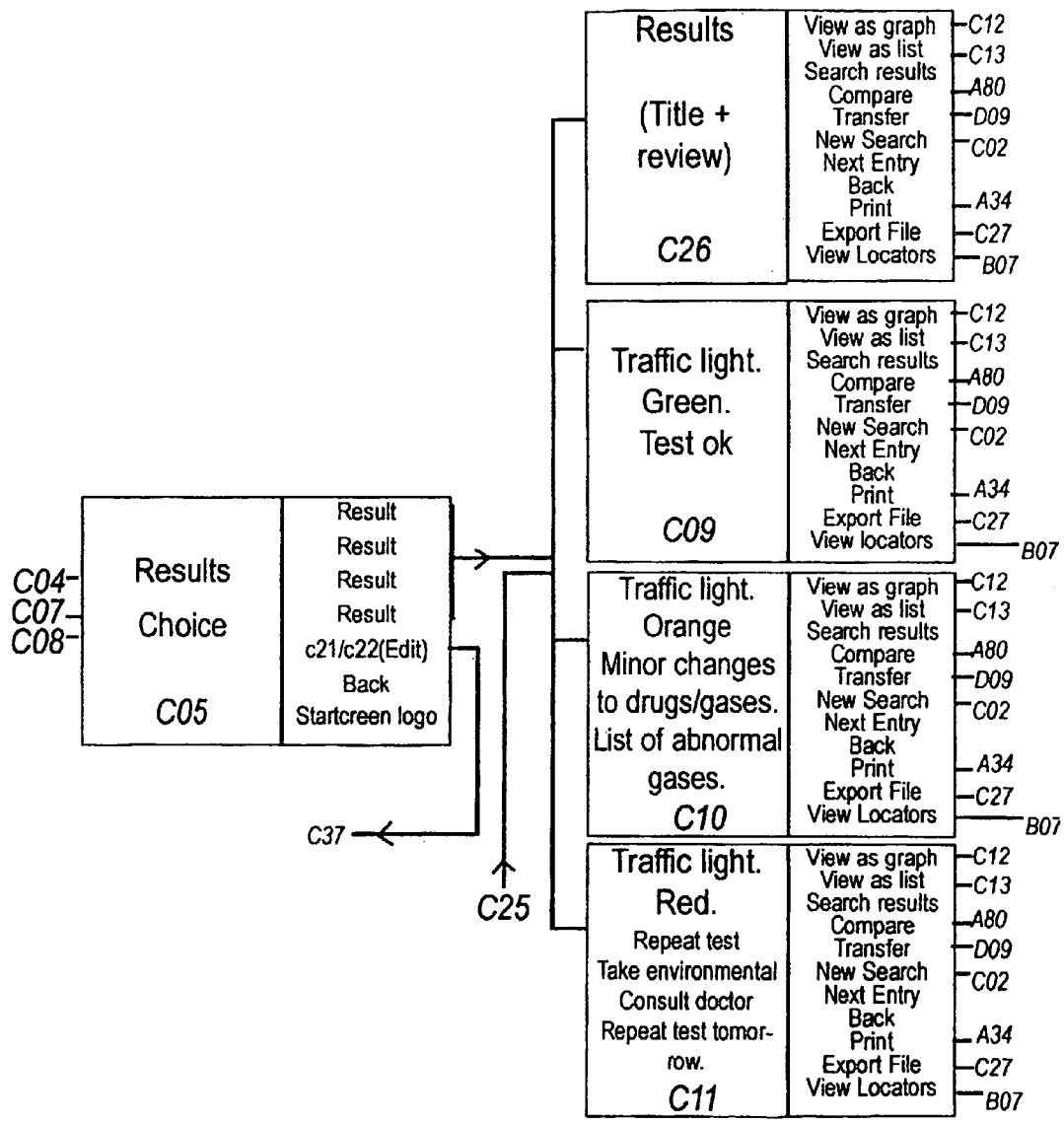
Figure 2T:
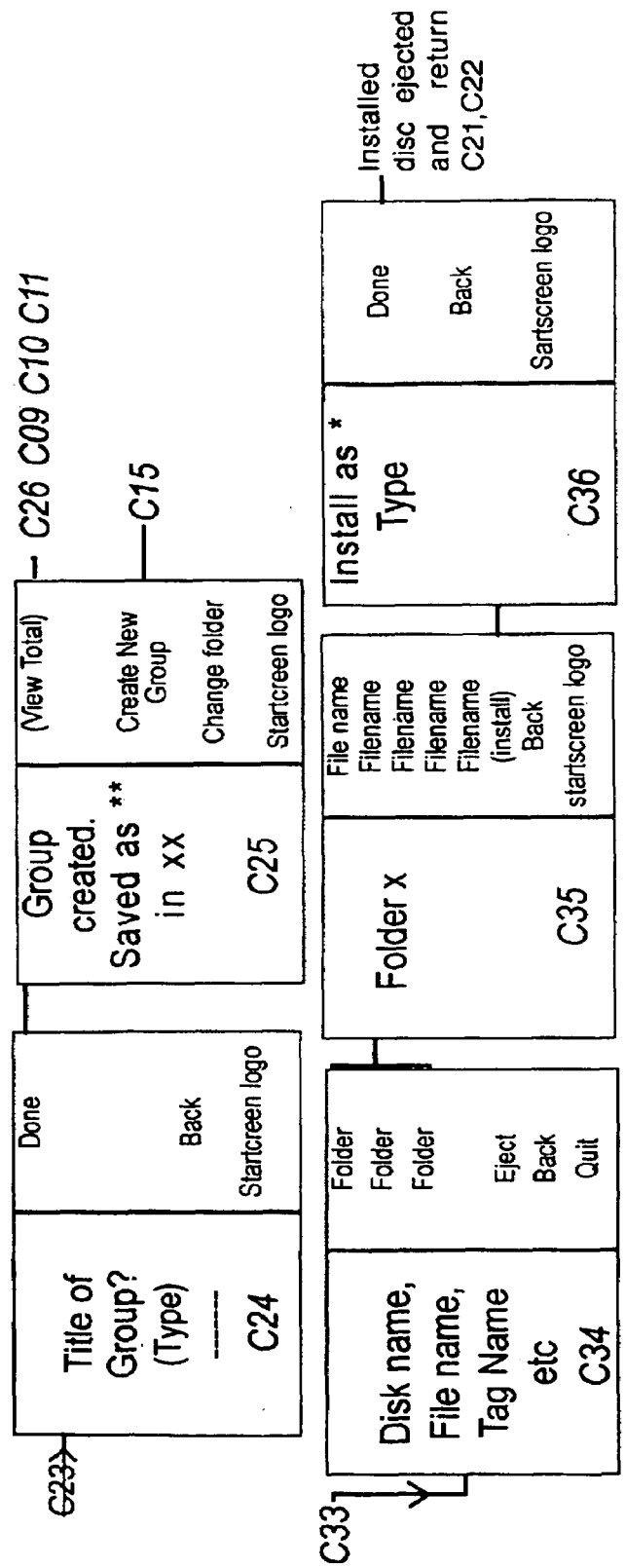
Figure 2U:
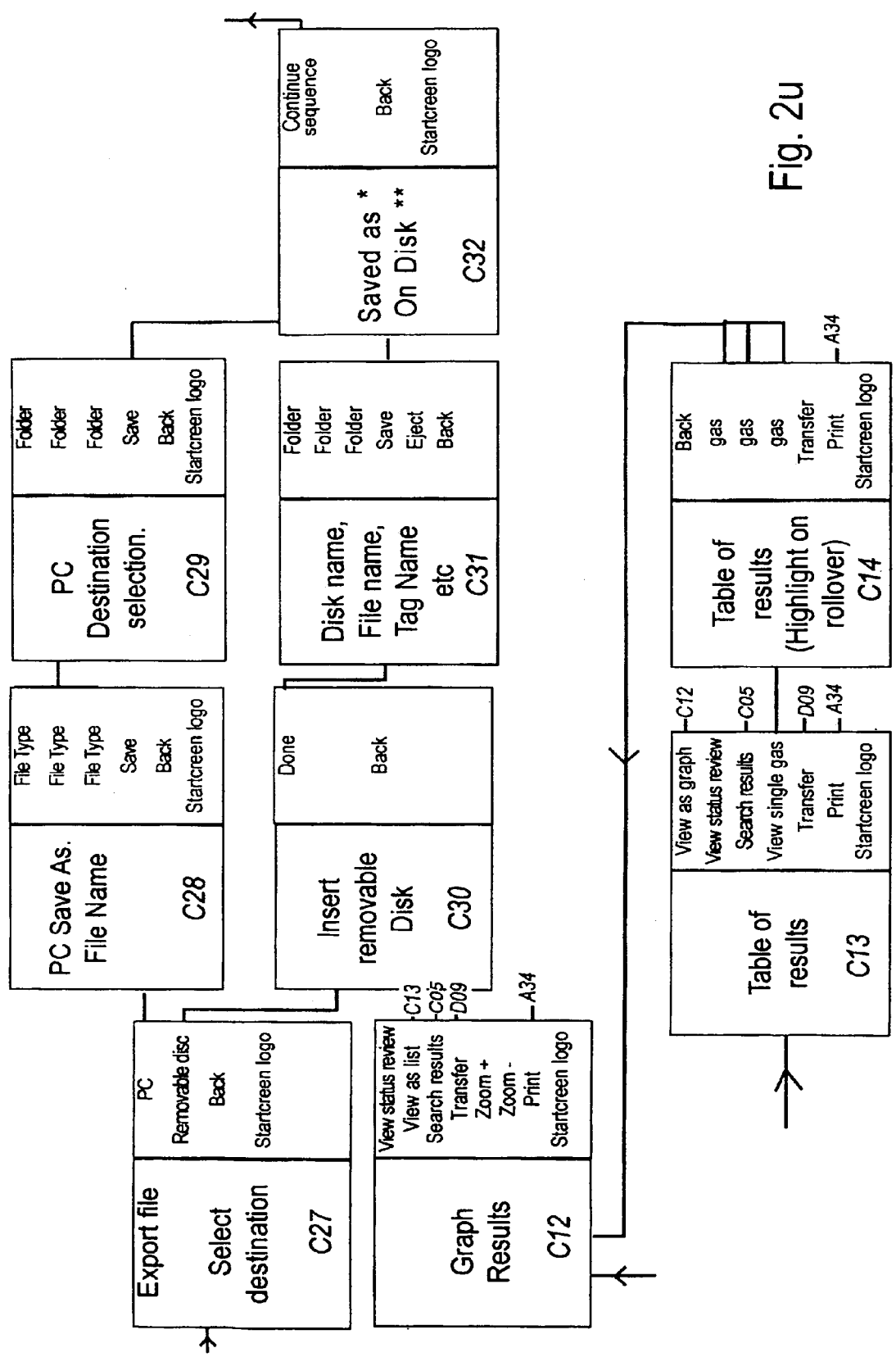
Figure 2V:
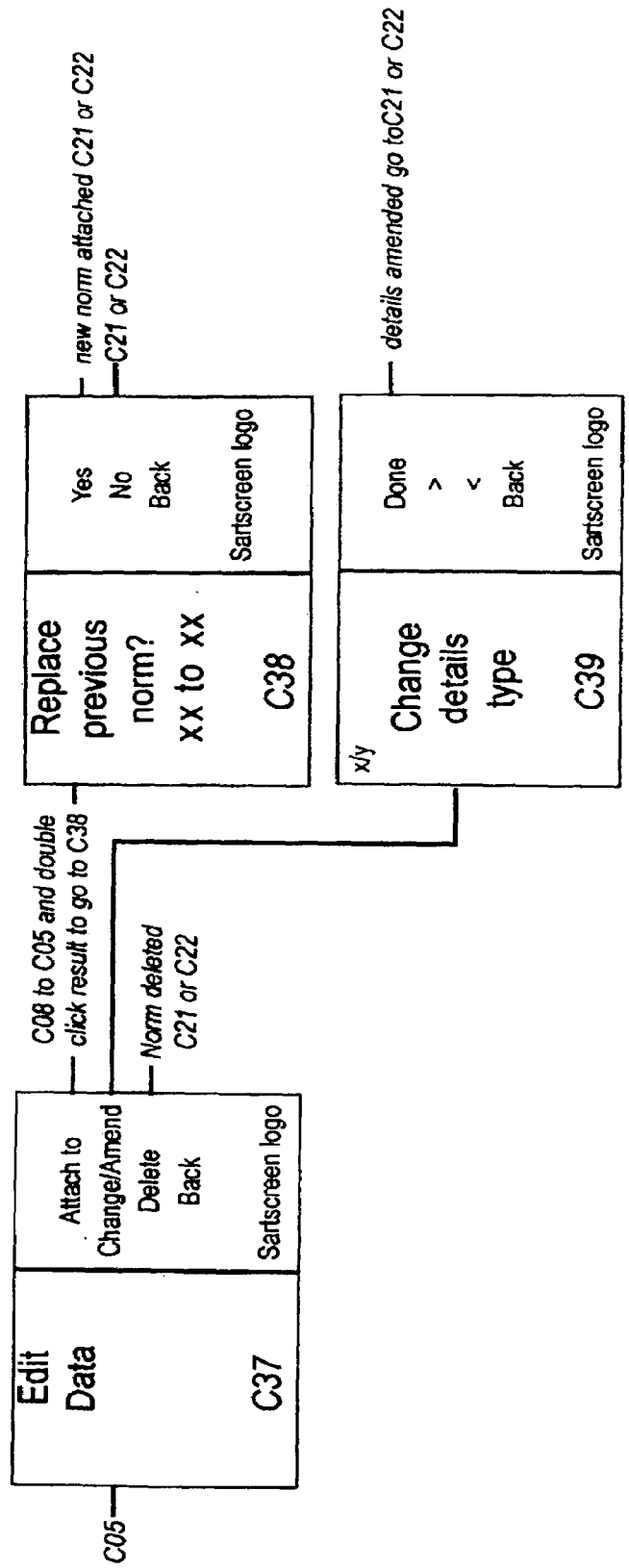

FIGS. 2a through 2v illustrate how the information obtained by the analysis can be used as a health diary. For example the analyzer may be provided with alarm indicators (referred to as traffic lights in FIG. 2a through 2v), which are activated if unusual or dangerous fluids or quantities of fluids are detected. Furthermore, the analysis may be compared with previously stored personal data to enable any changes to be identified.

The information obtained can then be stored and tagged for subsequent use for instance in forensic operations. The results can also be compared with existing data. Alternatively the data can be interpreted to provide warnings of the presence of dangerous fluids, environmental changes leading to storms and earthquakes and other natural phenomena. Alternatively the data can be interpreted for medical purposes for the diagnosis of illnesses and the prescription of medicines as an advisory system. The information can also be used to give a particular signature to the source of the sample for example; the accuracy of the techniques of the present invention enables unique individual breath signatures to be obtained somewhat like an individuals DNA profile. Having a unique individual signature registered could be most useful in other areas such as security and personal identity ratification. Replicating the individual signature, that is specific fluids in their concentrations, will not be possible. The fluid analyser system may be used for the purpose of predictions. For example, indications from a trend or signature that a person may have an illness developing which could be prevented if identified at an early stage.

The Examples of additional data that may be stored include one or more of external data such as height, weight, age, body mass, body surface area, lung capacity, blood type, blood analysis including blood pressure, hydration levels, blood sugars, blood testosterone, blood oestrogen levels and cholesterol. Blood flow, chill factors, reflection, respiration rate, pulse, gender, ethnicity, posture, lifestyle, supplementary lifestyle, location, supplementary location, molecular size, molecular weight, gravity, activities and calorific values.

The fluid analyser system of the present invention can be used for clinical studies. In a study of Asthma, as one example of many, there would be a qualitative and/or quantitative difference not only between asthmatics and non-asthmatics but also between asthmatics of differing clinical manifestation, or variation within an individual sufferer on occasions of different physiological status. In this way the fluid analyser system will not only have the ability to screen for the presence of certain fluids associated with diseases or illnesses, but be able to monitor severity and long term fluctuation. In addition to the clear clinical diagnostic potential, the fluid analyser system will also be able to analyse components in the environment which may trigger or increase the risk of certain conditions, such as sensitising agents and allergens important to atopic excema, and other respiratory illnesses.

The results generated from the fluid analyser system can be used as markers. These markers will be known as signatures and can be used as overlays for comparative analysis by the users for status reports, acting as an advisory system only. Using the advisory data together with other outside information and technologies, the users have the potential to determine problems, diseases and illnesses, diagnosis, individual dosage, standards and prediction, designer medication, warnings and alarms, remedial actions and new fluids.

Another benefit of the fluid analyser system is that it is able to provide the user with instant data. The resulting advisory status report can be understood and appreciated by a wider user group immediately preventing event driven courses of action and decision making creating a more proactive approach.

Examples of the information that may be pre-recorded and put into the fluid analyser system's database for comparative analysis are as follows:

1. Known data taken as a standard of environmental and the individual norm for fluids. From 0- to 100% of normal volume with proposed splits of measurements to form a template. For example, Nitrogen is from 0- to 100% of normal volume with increments of at least 0.0000000001%.
2. Known physical environmental data extended up and down the normally accepted scales of measurement with further extensions both up and down the scale as found in artificial environments. From 0- to 100% of normal volume with proposed splits of measurements to form a template. For example, temperature is −100° C. to +100° C. with increments of 0.00001° C.
3. Known physical data tables of individuals recording all parameters also relating to breath gases extended up and down the normally accepted scales of measurement with further extensions both up and down the scale. From 0- to 100% of volume with proposed splits of measurements to form a template.
4. Recorded as actual measurements of the environment on the day (including temperature, pressure, humidity) and at the time of the collection of the sample. With the facility to overlay against the pre-recorded known data listed above under 1 to 3.

5. Recorded as actual individual physical tests on the day and at the time of the environmental test. With the facility to overlay against the pre-recorded known physical data listed under 1 to 4.

6. Databank of known wavelengths of fluids. Any methodology may be used to add a new fluid to the database. However, we prefer to set the temperature of the fluid system analyser, record measurements of what is present in the consistent light environment chamber without the receptacle inside, under a pre-determined time duration. Using the Radiation Absorbance Device(s) (RAD) receive and absorb, radiation from the radiation source and record the values measured. The radiation source is the atmosphere and its surroundings within the consistent light condition environment. Next the receptacle is filled with the pure fluid, Nitrogen gas for example, and placed into the consistent light condition environment and the temperature set. Under a pre-determined time duration, the fluid analyser system's Radiation Absorbance Device(s) (RAD) receive by absorbance, radiation from the, Nitrogen, which is known wavelengths. Through standard curve fitting techniques the values are magnified enabling a clearer definition as to the identity of the wavelengths and their peak intensity values. Repeating the process any number of times will provide an increased accuracy through averaging. What is considered to be distortion and noise via a process of elimination referencing other known data, such as the impact of the receptacle itself and the light environment compartment, and samples taken, the remaining peak intensity wavelength values provide an identity. In this example, Nitrogen.

7. Actual wavelengths act as indicators to mark their peak intensity measurements. Where the intensities peak, the corresponding wavelengths are matched against the databank, established as set out in 6 above, of known wavelengths of fluids. Matching wavelengths within a pre-defined tolerance will determine the presence of an individual fluid. This process is repeated automatically until all fluids stored in the databank have been searched and the fluids in the sample identified. Points 4, 5 and 8 relate to and/or incorporate 7 via their definitions.

8. Actual absorbance data of intensities to determine volumes of identified fluids. When used for health purposes this can illustrate excesses and depletions of the norm and/or trends.

The content of the sample having been determined the software can be programmed to enable the following comparisons to be made:

A. The data recorded under 4 above is compared with the data under number 1. With a list of numerical comparatives and +/−% variances shown. With numerous tests per individual, a trend or more accurate mean and degree of +/−% variance of the extrapolated data can be established against the norm listed in the pre-recorded data of 1 above.

B. The data recorded under number 5 above is compared with the data under number 1. With a list of numerical comparatives and +/−% variances shown. With numerous tests per individual, a trend or more accurate mean and degree of +/−% variance of the extrapolated data can be established against the norm listed in the pre-recorded data of 1.

C. The data recorded under number 5 above is compared with the data under number 3. With a list of numerical comparatives and +/−% variances shown. With numerous tests per individual, a trend or more accurate mean and degree of +/−% variance of the extrapolated data can be established against the norm listed in the pre-recorded data of 3.

D. The data recorded under numbers 4 & 5 above is collectively to be compared with the data under numbers 3 & 2. Together with a list of numerical comparatives and +/−% variances shown. With numerous tests representing the samples, a trend or more accurate mean and degree of +/−% variance of the extrapolated data can be established against the norm listed in the pre-recorded data of 3. & 2.

E. The data recorded under number 4 above is compared with the data under number 2. Only with a list of numerical comparatives and +/−% variances shown. With numerous tests representing the sample, a trend or more accurate mean and degree of +/−% variance of the extrapolated data can be established against the norm listed in the pre-recorded data of 2.

F. The data recorded under numbers 1 & 4 is compared with the data under numbers 1 & 5. Only with a list of numerical comparatives and +/−% variances shown. With numerous tests representing the sample, a trend or more accurate mean and degree of +/−% variance of the extrapolated data can be established against the norm listed in the pre-recorded data of 2.

G. The data recorded under any of numbers 1, 2, 3, 4 or 5 may be compared with previous internal and/or external sample readings and/or data.

H. Historical number 1, 2, 3, 4 or 5 readings may be compared with previous internal and/or external sample readings and/or data.

I. The data recorded under number 5 may be compared with number 4., compared with previous internal and/or external sample readings and/or data.

J. Historical Number 5 may be compared with historical number 4., and may be compared with previous internal and/or external sample readings and/or data.

K. Including 7 and 8. Comparisons made from A, B, C, D, E, F, G, H, I and J or combinations of.

These comparisons are particularly useful if the fluid analyser is to be used for medical purposes monitoring human breath, for example, by comparing the actual results of the analysis of the individual's breath and the environment to the normal signature taken from their breath analysis and what is normally expected to be found in that environment, the fluid analyser system will provide data assisting in an independent diagnosis as to whether an individual's problem was triggered by the environment or not. This is achieved by carrying out comparative studies using the fluid analyser system software.

By using the fluid analyser system the user has the potential to determine through comparative analysis, for example, whether or not an athlete has been involved with performance enhancing drugs.

One of the primary uses is as a means of analysing collected fluid samples to detect and quantify specific compounds, or combination of compounds. The results generated can become markers. These markers will be known as signatures and can be used as overlays for comparative analysis by the users for status reports, acting as an advisory system only. Using the advisory data together with other outside information and technologies, the users can determine problems, diseases and illnesses, diagnosis, individual dosage, designer medication, warnings and alarms, standards and predictions, remedial actions and identify new fluids. The Fluid analyser system data can be made available to the end user within 1 minute.

A preferred form of a receptacle for use in the collection of samples for use in the present invention is shown in FIG. 3 which is a cross section of the receptacle in uninflated packed form. The receptacle which is preferably sterilised and vacuum packed to avoid contamination consists of a top (1) on which is mounted a non-return valve (2) and a conduit (3) through which the fluid sample may be supplied. The flexible sample bag (4) is collapsed and is sealed/attached at the base and the top.

FIG. 4a is the side elevation and shows the receptacle inflated with the fluid sample. FIG. 4b is the front elevation, which also shows the receptacle inflated with the fluid sample.

To use the receptacle, the vacuum packed seal(s) is broken, the source of the fluid applied to the chosen orifice and the sample collected through the conduit (3 of FIG. 3) from the pressure of the flow of exhalation and/or emission: or alternatively through the conduit (3 of FIG. 3) to retrieve a collected sample from the environment. This may be achieved by pulling the base away from the top (1) releasing valve (2) until the receptacle, FIG. 3, is fully inflated, as shown in FIG. 4. The valve automatically returns to its closed position once the receptacle is fully inflated or the motion of pulling the base away from the top stops. To use the receptacles in FIGS. 5, 6 and 7 the same methodology can be applied.

The receptacle enables a non-pressurised sample collection method due to the fact there is no additional power or assistance required other than that of the flow of the fluid being collected and/or pulling motion, maintaining the integrity of the sample. The receptacle once full, as shown in FIG. 4, is sealed with valve (2) and therefore is unable to pollute the fluid analyser system. The receptacle is preferably used only once to maintain the integrity of the collected sample, it can then be disposed of carefully or the individual components making the receptacle can be disconnected for recycling.

If, as in one example, the collected sample is to be stored for long periods of time prior to analysis, a screw cap of some description which may be fluorinated may be used to further prevent contamination of the sample. To attach the screw cap, the thread of the valve holder may be used.

Figure 10:
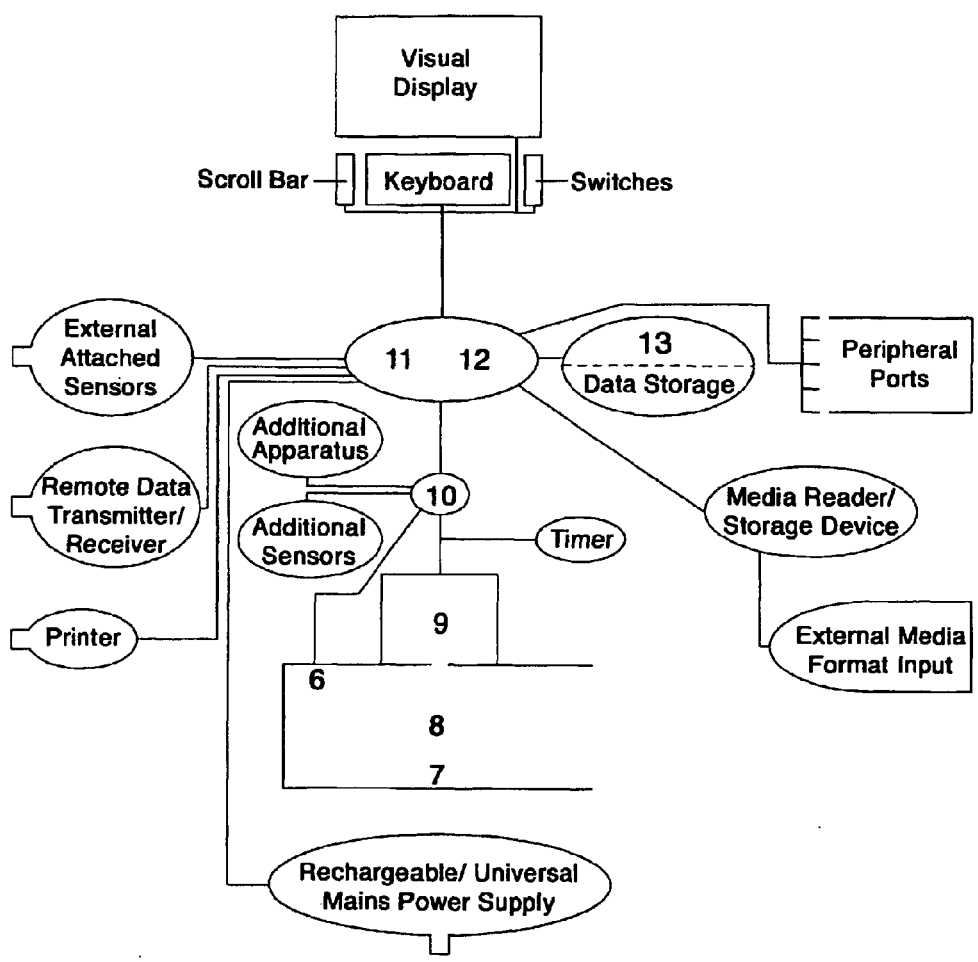
FIG. 10 is a diagrammatic illustration of the apparatus of the present invention.

FIG. 10 is a diagrammatic illustration of the apparatus of the present invention. The apparatus consists of a consistent light environment chamber (6) into which the inflated receptacle of FIGS. 4, 5, 6 or 7 can be fully inserted. The apparatus is provided with a lid (not shown) so that when closed the consistent light environment chamber and the inflated receptacle remain in a controlled light environment. The apparatus is provided with sensors (7) which determine the temperature in the consistent light environment chamber, the temperature of the fluid sample and the level of light.

The analysis process can be activated through the interface controller (10) which, simultaneously activates a timer. Once the radiation absorption device(s) (9) are activated, they start recording the radiation from the sample (8) and the timer records the duration of the measurement which stops once the pre-determined duration time has elapsed. The measurement concerning the intensity levels detected by the RAD(s) at known wavelengths is transferred to a computer system (11) and (12) where the signal is translated and magnified. The peak intensity wavelengths are then identified and transmitted to be referenced against a database (13) of known data of wavelengths of fluids to determine the identity of fluids present. The computer (11) also provides means for calculating the total and individual volumes of fluids present referenced against the known volume of the receptacle and the process variables.

Preferably, the present invention consists of the rest of the apparatus or combinations thereof shown in FIG. 10.

In addition to the fluid analyser system having the ability to be linked to multiple fluid analyser systems or peripheral devices for the purpose of transferring, comparing, referencing and/or using data multiple fluid analyser systems may be present in one form. For example, there may be any number of light consistent environment chambers (6), sensors (7), RADs (9), configured in the same arrangement as FIG. 10 linked into the computer system (10), (11), (12) & (13) to analyse collected samples (8). The collected samples' measurements can be recorded singly, simultaneously or in combinations thereof through controller (10). Additionally, different types of fluid receptacles may be used at anyone time or combinations thereof to determine a variety of environmental conditions within a particular site. The respective light consistent environment chambers are able to receive the differently shaped fluid receptacles accordingly. This flexibility allows for multitasking to be completed utilising just one Fluid analyser system with all work being carried out at the same time.

Figure 11:
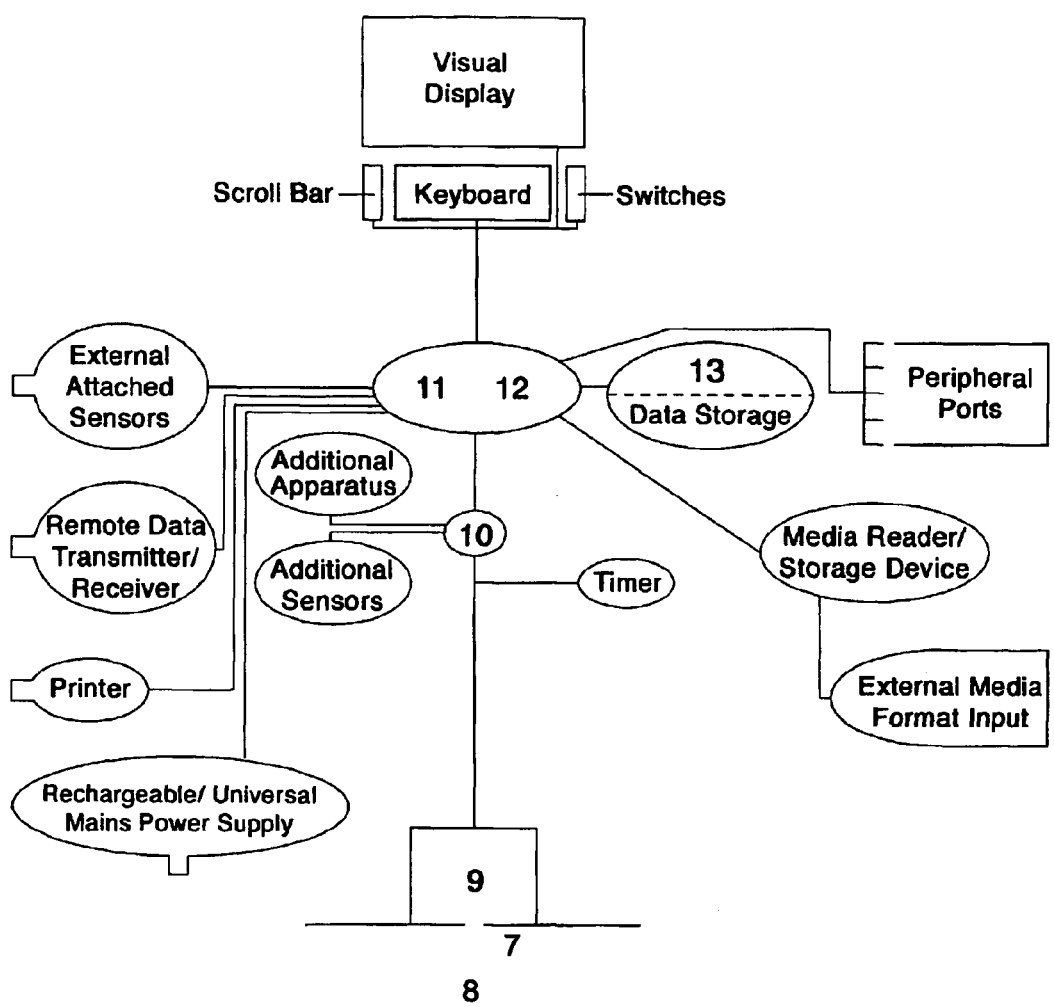
FIG. 11 is a diagrammatic illustration of an alternate apparatus of the present invention.
Figure 13:
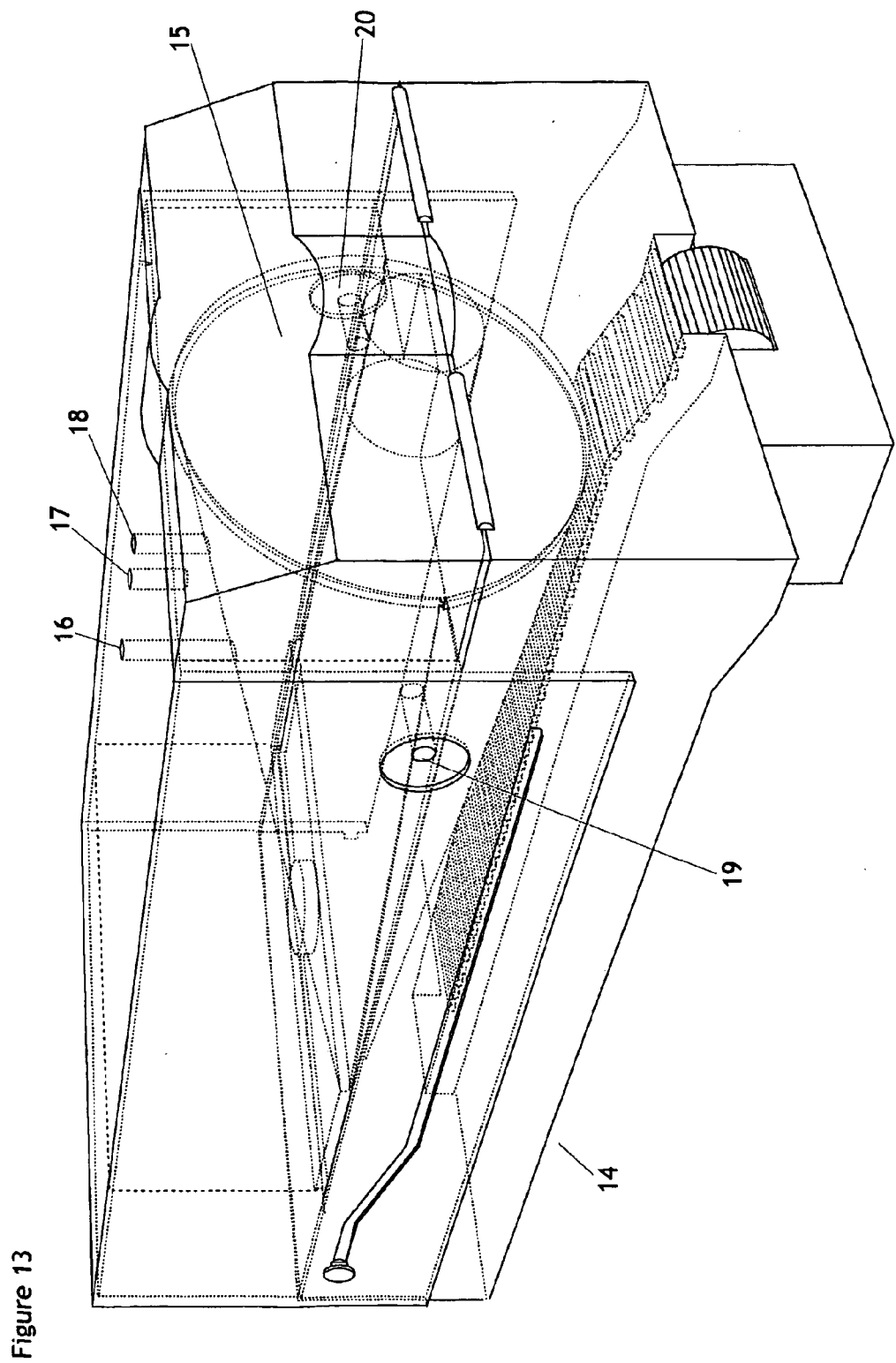
FIG. 13 is a cut away view of the compartment of an analyser according to the present invention which shows a housing (14) in which is a compartment (15) for receipt of the receptacle containing the sample to be analysed. The compartment may be removable and replaceable to accommodate different receptacle shapes and sizes such as FIGS. 4,6 and 7. A light sensor (16), an ambient environment temperature measurement (17) and a sensor (18) for measuring the sample temperature are provided. In addition the wall of the compartment is provided with detectors (19) and (20) which, in a preferred embodiment, are multiple CCD fittings. The compartment as shown in FIG. 13 may then be connected to a recorded device such as that illustrated in FIG. 15.
Figure 14:
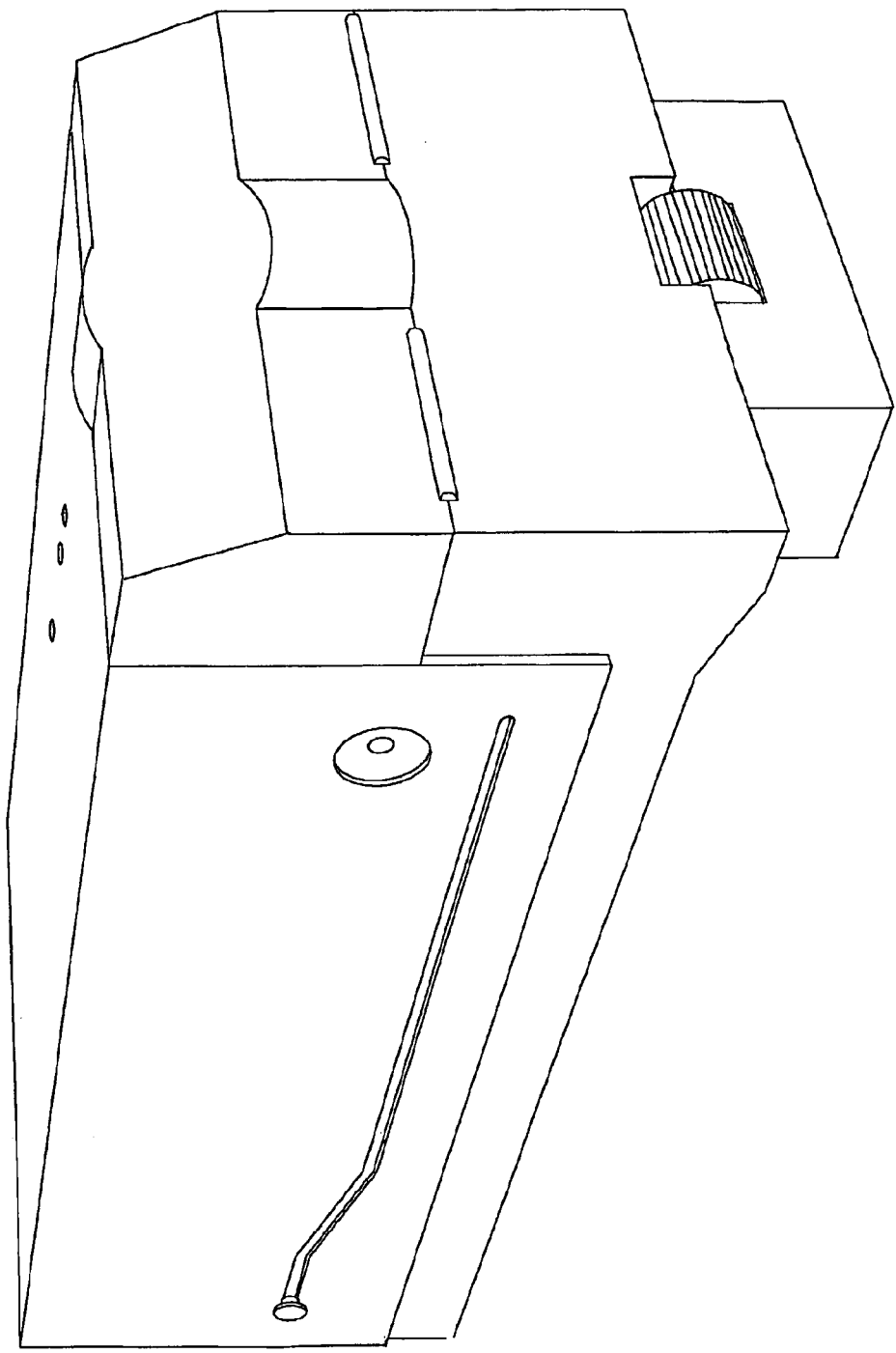
FIG. 14 is a view of the consistent light environment compartment.
Figure 15:
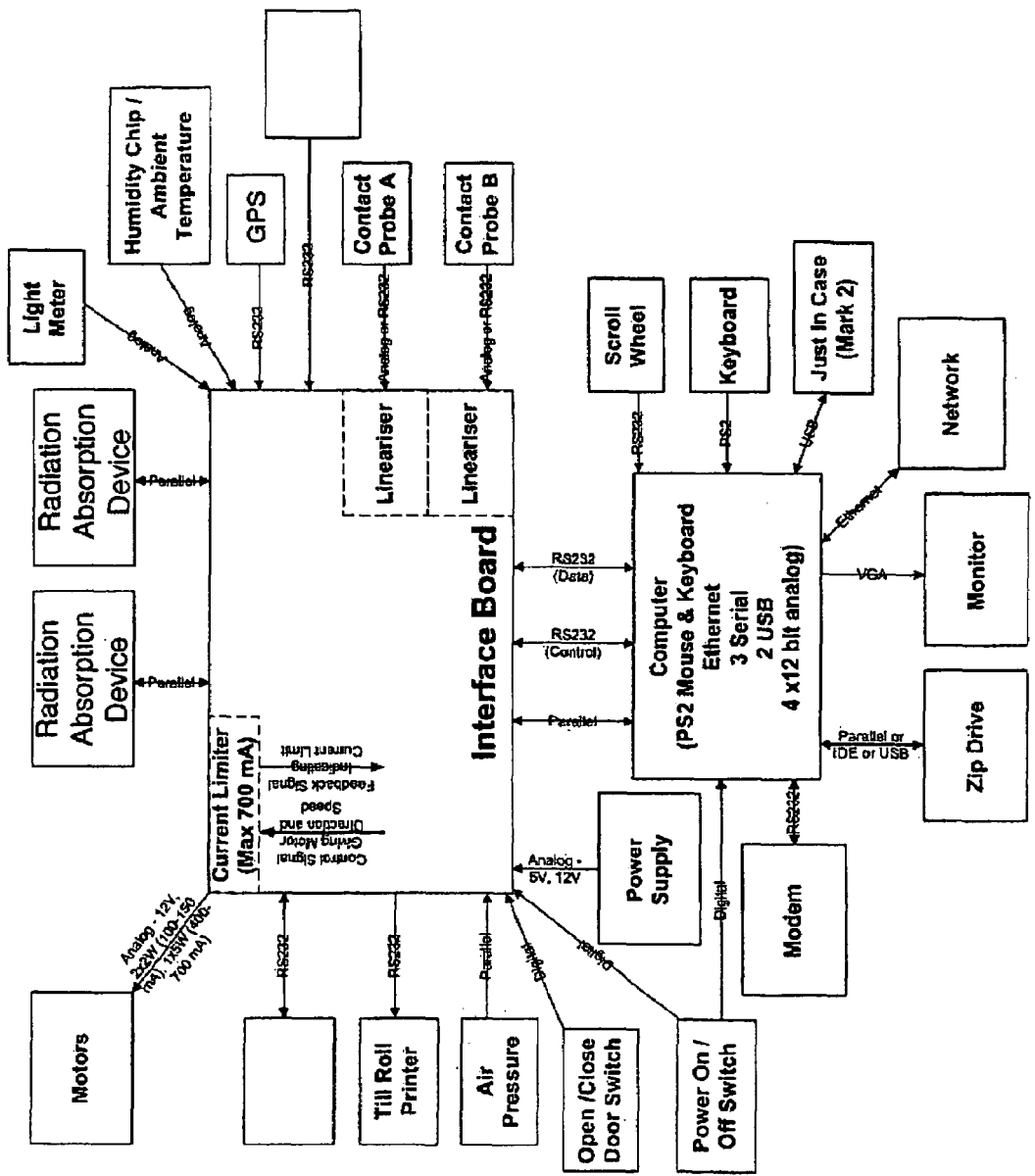
FIG. 15 is a schematic illustration of the data recorder and database that may be associated with the compartment of FIG. 13. The interface board shown may have other interface boards of the same or differing arrangements connected.

Furthermore, for identification purposes only, it is possible by different arrangement of the fluid analyser system to identify the content of individual fluids in the outer environment where the fluid analyser is located. In FIG. 11, the RAD(s) (9) are positioned in such a way that the radiation source (8), is the atmosphere or other fluid sample of the environment. This fluid analyser system may be used for the purpose of determining whether a particular dangerous or potentially hazardous gas or gases are present in the atmosphere in which people need to operate, for example.

Staged timing throughout a 24 hour day using multiple sample containers inserted within the controlled environment chambers for automatic monitoring of the climatic register of the atmosphere will record regular comparative data altered by time and the process variables within the current environment.

All data received from the fluid analyser system sensors is either magnified and/or averaged via multiple sampling to a greater degree of accuracy.

The invention claimed is:

1. A fluid analyser system for measuring radiation emitted by a fluid sample comprising:
   i) a sealed receptacle containing only the fluid sample;
   ii) a consistent light condition chamber in which the receptacle is placed;
   iii) a timing device for measuring duration of the scan of the radiation emitted by the fluid sample in the receptacle;
   iv) a temperature sensor for determining the temperature of the fluid sample;
   v) at least one detector that detects the radiation emitted by the fluid sample, said at least one detector being located at a predetermined distance from the fluid sample; and
   vi) means for translating and magnifying the signal from the at least one detector and enabling identification of the intensities and the peak intensity values wavelengths of the radiation emitted by the fluid sample, wherein the fluid sample is non-invasively analysed.

2. A fluid analyser system according to claim 1 also containing a light meter for determining the consistent light condition environment.

3. A fluid analyser system according to claim 1, containing means whereby the peak intensities and peak intensity values are summed and/or correlated with known/unknown peak intensities and/or peak intensity values (nm wavelength values) to indicate the nature of the fluids present in the fluid sample and to determine the concentrations of the fluids in the fluid sample.

4. A fluid analyser system according to claim 1 operated via a computer driven software system which provides an advisory status report of the content of the fluid and the conditions under which the test was performed.

5. A fluid analyser system according to claim 1 including a means for the measurement of the humidity and dew point of the fluid sample.

6. A fluid analyser system according to claim 1 including means for determining the atmospheric pressure.

7. A fluid analyser system according to claim 1, further comprising a GPS.

8. A fluid analyser system according to claim 1 including a means for the measurement of one of more of velocity, sound, gravity and vibration.

9. A fluid analyser system according to claim 1 in which the walls of the receptacle have a high optical clarity and are flexible but not elastic.

10. A fluid analyser system according to claim 1 in which the receptacle is formed from a fluorocarbon polymer.

11. A fluid analyser system according to claim 1 in which the receptacle is provided with a one-way valve.

12. A fluid analyser system according to claim 11 in which the valve is in a valve holder which is shaped so that a fluid delivery tube can be attached to the top of the receptacle.

13. A fluid analyser system according to claim 1, in which the shape of the inflated receptacle is such that it is a firm fit within the consistent light condition environment.

14. A fluid analyser system according to claim 1, wherein said chamber containing a mechanism that permits a temperature probe to be inserted through a wall of the chamber to touch a surface of the receptacle whereby the probe measures a temperature of said fluid sample without penetrating the surface of the receptacle.

15. A fluid analyser system according to claim 14 in which the mechanism driving the temperature probe is controlled by variable resistance ensuring for each time the probe is positioned it will be encased by the receptacle but penetration of the receptacle is prevented.

16. An analyser system according to claim 1 in which the analyser system is non-invasive.

17. An analyser system according to claim 1 that operates and transmits/receives test data remotely.

18. An fluid analyser system according to claim 1 including one or more of a visual display screen, a printer, a data transmitter/receiver, data storage, rechargeable/universal mains power supply, peripheral ports, keyboard, scroll bar, switches.

19. A fluid analyser system according to claim 1, further comprising a database of fluids and their known wavelengths, that are compared to wavelengths of the detected radiation of the fluid sample.

20. A fluid analyser system according to claim 1 adapted to provide a comprehensive advisory status report of the fluids analysed with the appropriate reference data.

21. An analyser system according to claim 1 in which the consistent light environment chamber is made of a single material.

22. An analyser system according to claim 21 in which the chamber is formed from a medical grade polypropylene.

23. An analyser system according to claim 1, wherein the walls of the sealed receptacle are of a material that has a solar transmission greater than 90%.

24. An analyser system according to claim 1, wherein said at least one detector is a radiation absorbance device.

25. An analyser system according to claim 1, wherein said receptacle has a cylindrical shape at the point where said at least one detector is positioned.

\* \* \* \* \*